United States Patent
Imagawa et al.

(10) Patent No.: US 7,351,551 B2
(45) Date of Patent: Apr. 1, 2008

(54) ADIPOCYTE DIFFERENTIATION-ASSOCIATED GENE AND PROTEIN

(75) Inventors: Masayoshi Imagawa, Aichi (JP); Yuichi Oku, Ibaraki (JP)

(73) Assignee: Nissui Pharmaceutical Co., Ltd., Toshima-ku, Tokyo (JP)

( * ) Notice: Subject to any disclaimer, the term of this patent is extended or adjusted under 35 U.S.C. 154(b) by 393 days.

(21) Appl. No.: 10/497,493

(22) PCT Filed: Dec. 5, 2002

(86) PCT No.: PCT/JP02/12747

§ 371 (c)(1),
(2), (4) Date: Jun. 3, 2004

(87) PCT Pub. No.: WO03/048358

PCT Pub. Date: Jun. 12, 2003

(65) Prior Publication Data

US 2005/0164183 A1    Jul. 28, 2005

(30) Foreign Application Priority Data

Dec. 7, 2001  (JP) .............................. 2001-374785

(51) Int. Cl.
*C12P 21/06* (2006.01)
*C12N 15/00* (2006.01)
*C12N 1/20* (2006.01)
*C07K 1/00* (2006.01)
*C07H 21/02* (2006.01)
*C01Q 1/68* (2006.01)

(52) U.S. Cl. ............... 435/69.1; 435/252.3; 435/320.1; 435/6; 530/350; 536/23.1

(58) Field of Classification Search ............... 536/23.1, 536/23.2; 435/69.1, 320.1, 252.3, 6; 530/350
See application file for complete search history.

(56) References Cited

U.S. PATENT DOCUMENTS 5,789,165 A    8/1998   Oku et al. .................... 435/6

FOREIGN PATENT DOCUMENTS

| EP | 0905517 | 3/1999 |
|---|---|---|
| JP | 6-003358 A | 1/1994 |
| JP | 8-333394 A | 12/1996 |
| JP | 9-292397 | 11/1997 |
| JP | 10-253632 A | 9/1998 |
| JP | 11-075865 A | 3/1999 |
| WO | WO 01/75054 | 11/2001 |

OTHER PUBLICATIONS

Carninci et al., 10, 1617-1630, 2000.*

(Continued)

*Primary Examiner*—Maryam Monshipouri
(74) *Attorney, Agent, or Firm*—Bacon & Thomas, PLLC

(57) ABSTRACT

Polynucleotides which are produced by preadipocytes within 12 hours from the start of adipocyte differentiation induction and comprise a base sequence identical or at least 93% homologous to SEQ ID NO:1, or a base sequence identical to SEQ ID NO:9, or polynucleotides complementary to those polynucleotides, and proteins comprising an amino acid sequence identical or at least 96% homologous to the protein shown under SEQ ID NO:2 or comprising the amino acid sequence shown under SEQ ID NO:10 are provided.

22 Claims, 5 Drawing Sheets

OTHER PUBLICATIONS

Bair et al., Database UniProt, Accession No. Q91Y26.*
Nature, vol. 372, Dec. 1, p. 425 (1994), Y. Zhang et al.
Molecular Cloning 2nd, p. 11.2-11.61, Cold Spring Harbor Laboratory Press (1989), J. Sambrook et al., section 11.2-11.61.
Nucleic Acids Research, vol. 9, No. 2, p. 309 (1981), J. Messing et al.
Proc. Natl. Acad. Sci., vol. 60, p. 160 (1968), Brooks Low.
J. Molecular Biology, vol. 120, p. 517 (1978), L. Clark et al.
J. Molecular Biology, vol. 41, p. 459 (1969), H.W. Boyer et al.
Genetics, vol. 39, p. 440, Jul. 1954, R.K. Appleyard.
Gene, vol. 24, p. 255 (1983), K. Yoshimura et al.
J. Biochem., vol. 95, p. 87, (1984), K. Ohmura et al.
In Vitro, vol. 13, No. 4, p. 213 (1977), J.L. Vaughn et al.
Nature, vol. 315, p. 592 (1985), S. Maeda et al.
Proc. Nat. Acad. Sci. USA, vol. 69, No. 8, p. 2110 (1972), S.N. Cohen et al.
Gene, vol. 17, p. 107 (1982), J.D. Reid et al.
Molec. Gen. Genet, vol. 168, p. 111, (1979) S. Chang et al.
Methods in Enzymology, vol. 194, p. 182, (1991), D.M. Becker et al.
Proc. Natl. Acad. Sci. USA, vol. 75, No. 4, p. 1929 (1978) A. Hinnen et al.
Bio/Technology, vol. 6, p. 47 (1988), V.A. Luckow et al.
Protocols for cell engineering experiments, p. 260-272, Anticancer Study Department, Inst. of Medical Sci., the University of Tokyo Editing Syuujyun-sha press and its English abstract.
Virology, vol. 52, p. 456 (1973), F.L. Graham et al.
Experiments in Molecular Genetics, p. 431-435, Miller, Cold Spring Harbor Laboratory, New York (1972).
Nature, vol. 195, Aug. 25, p. 788 (1962), T.D.C. Grace.
Science, vol. 122, No. 3168, Sep. 16, p. 501 (1955), H. Eagle.
Virology, vol. 8, No. 3, p. 396, (1959), R. Dulbecco et al.
The Journal of the American Medical Association, vol. 199, No. 8, p. 519, (1967), G.E. Moore et al.
Proceedings of the Society for Experimental Biology and Medicine, vol. 73, January, p. 1 (1950), J.F. Morgan et al.
http://www.invitrotech.co./jp/about_cellfree_e.html.
Proc. Natl. Acad. Sci. USA, vol. 87, March, p. 1663 (1990), R.N.V. Gelder et al.
Nature Genetics Supplement, vol. 21, January, p. 33 (1999), P.O. Brown et al.
Nature Biotechnology, vol. 17, April, p. 365 (1999), P.N. Gilles et al.
http://www.prosequencing.com/pages/technology_content.html.
Transfusion, vol. 36, No. 5, p. 426 (1996), T.J. Legler et al.
Cytometry, vol. 39, p. 131 (2000), M.A. Iannone et al.
"Surface Plasmon Resonance," Technology Note 1, http://www.biacore.co.jp.
Journal of Neurochemistry, vol. 56, No. 2, p. 560 (1991), H. Okano et al.
Nucleic Acids Research, vol. 6, No. 9, p. 3073 (1979), J.S. Lee et al.
Science. vol. 241, Jul. 22, p. 456, (1988), M. Cooney et al.
Science, vol. 251, Mar. 15, p. 1360 (1991), P.A. Beal et al.
Human Molecular Genetics, Chapter 20, p. 551-587 (1996), T. Strachan et al.
Zhao L. et al., Transient Induction of ENC-1, a Kelch-related Actin-binding Protien, Is Required for Adipocyte Differentiation. J. Biol. Chem., Jun. 2, 2000, vol. 275, No. 22, pp. 16845- to 16850.
Albreksen T. et al., Identification of a Novel Integral Plasma Membrane Protein Induced During Adipocyte Differentiation. Biochem. J., Oct. 15, 2001, vol. 359, No. (pt 2), pp. 393 to 402.
Moldes M. et al., Molecular Cloning of a Major mRNA Species in Murine 3T3 Adipocyte Lineage. Differentiation-dependent Expression, Regulation, and Identification as Semicarbazide-sensitive Amine Oxidase. J.Biol.Chem., Apr. 2, 1999, vol. 274, No. 14, pp. 9515 to 9523.
Albrektsen T. et al., The Transcription Factor Fos-related Antigen 1 is Induced by Thiazolidinediones During Differentiation of 3T3-L1 cells. Mol. Pharmacol., Mar. 2001, vol. 59, No. 3, pp. 567 to 575.
Nishizuka, M et al, "RGS2 Promotes Adipocyte Differentiation in the Presence of Ligand for Peroxisome Proliferator-activated Receptor Gamma," The Journal of Biological Chemistry. , Ausgust 10, 2001, pp. 29625-29627.
Heath, P., "Humman DNA Sequence from Clone RP11-146P21 on Chromosome 10 Contains the 3' End of the a Novel Gene, the 5' End of a the Gene for KIAA0608 and a CpG Island.", May 5, 2000, Database EMBL "Online", XP002317667.
Imagawa, M et al, "Identification of Inducible Genes at the Early Stage of Adipocyte Differentiation of 3T3-L1 Cells,", Biochemical and Biophysical Research Communications, Jan. 19, 1999, vol. 254, No. 2, pp. 299-305.
Tominaga, K. et al, "Fad24, A Mammalian Homolog of Noc3p, is a positive Regulator in Adipocyte Differentiation.", Journal of Cell Science, Dec. 1, 2004 pp. 6217-6226.
J.J. Doyle, et al. "Evolution of genes and taxa: a primer", Plant Molecular Biology, 2000, vol. 42, pp. 1-23.
Proc. Natl. Acad. Sci. USA, vol. 77, No. 8, p. 4504 (1980), K.A. Bostian et al.
Proc. Natl. Acad. Sci. USA, vol. 81, September, p. 5330 (1984), G.A. Bitter.

* cited by examiner

Clone 24

(a) Whole cell (b) DAPI (c) GFP

Ectopic clone 24
expression
NIH3T3

Control

ADIPOCYTE DIFFERENTIATION-ASSOCIATED GENE AND PROTEIN

CROSS-REFERENCE TO RELATED APPLICATIONS

This application is a National Phase Application (35 USC 371) of PCT/JP02/12747 and claims priority of Japanese Application No. 2001-374785 filed Dec. 5, 2001.

TECHNICAL FILED

This invention relates to a polynucleotide designated as "clone 24 polynucloetide", which is expressed in the early stage of adipocyte differentiation and, a protein designated as "clone 24 protein" and, further, to an antibody, an antagonist and an agonist to or of the clone 24 protein, to the production of these, and to a pharmaceutical composition and a diagnostic agent containing any of the substances enumerated above.

BACKGROUND ART

Obesity resulting from supernutrition is now the most important factor causing such severe lifestyle-related diseases as diabetes, hypertension and arteriosclerosis. In considering the future life sciences and health sciences, the elucidation of the molecular mechanisms of obesity may be said to be an essential task. It is adipocytes that are directly involved in obesity, and the elucidation of the process of adipocyte generation, if given, will have a direct bearing on the treatment of obesity. With the recent advances in molecular biology, the mechanisms of adipocyte differentiation are being elucidated. It is known that there are a group of key genes and that these form an ingenious information-exchanging network.

The adipocyte differentiation process comprises a complicated series of steps, and adipoblasts differentiate into preadipocytes, which then differentiate into adipocytes. Transcription factors closely related to adipocyte differentiation have recently been discovered in systems using cultured cells or genetically modified individuals, for instance.

PPARs (peroxisome proliferator-activated receptors), the C/EBP (CCAAT/enhancer-binding protein) family and SREBP-1/ADD1 (sterol regulatory element binding protein 1 or adipocyte determination and differentiation-dependent factor 1) are said to be most important transcription factors in adipocyte differentiation.

It has been made clear that PPARs form a family, in which PPARγ is especially important for adipocyte differentiation. Thus, it has been made clear that ectopic expression of PPARγ results in differentiation of adipoblasts and preadipocytes into adipocytes. This result may be said to be evidential of the fact that PPARγ plays an important roll in adipocyte differentiation.

Like PPARs, C/EBPs form a family and, recently, it has been found that C/EBPα, like PPARγ, functions as a master regulator in adipocyte differentiation. Further, C/EBPβ and C/EBPδ are considered to be expressed in the early stage of differentiation, controlling the expression of C/EBPα and PPARγ.

While SREBP1/ADD1 is known to promote the differentiation of adipocytes, it has also been demonstrated that it is involved in PPARγ ligand formation in the process of adipocyte differentiation.

It has been demonstrated that the above-mentioned three transcription factor groups (PPAR, C/EBP, SREBP1/ADD1) make crosstalks, whereby the differentiation process goes on.

It has been demonstrated that the expression of the above three transcription factor groups increases from the relatively early stage of adipocyte differentiation. They are regarded as master regulators controlling the expression of a plurality of target genes. It is known that when these transcription factors are considered from the expression stage viewpoint, the expression of C/EBPβ and C/EBPδ increases in the relatively early stage. However, what gene or genes are activated in the earliest stage of differentiation of preadipocytes into adipocytes, namely within a half day (12 hours) from the start of differentiation, has been little clarified.

Analyses and/or specification as to whether the genes activated in the earliest stage of differentiation of preadipocytes into adipocytes, namely within 12 hours from the start of differentiation, are expressed or not, the levels thereof, the occurrence or nonoccurrence of proteins as gene products, the amounts thereof and the sites of expression thereof, if the genes are expressed, as well as gene mutation analysis may serve to provide factors very important in elucidating the mechanisms of obesity, further understanding the progressive state of obesity properly, and making use of the thus-obtained findings in the prevention or treatment of obesity. For that purpose, it is desirable to identify such genes as well as the proteins, which are products of such genes, and detect or assay such genes or proteins.

Accordingly, it is an object of the present invention to find out a gene capable of being activated within 12 hours from the start of differentiation of preadipocytes into adipocytes and provide a vector containing that gene, a transformant harboring that vector, a protein produced from that transformant, an antibody specific to that protein, a method of producing that protein, an agonist or antagonist to that protein, a pharmaceutical composition or diagnostic composition containing one or more of such compounds.

DISCLOSURE OF THE INVENTION

The present inventors made intensive investigations in an attempt to accomplish the above object and, as a result, they carried out cloning by the subtractive method for the points in time before induction of adipocyte differentiation and 3 hours after induction using murine 3T3-L1 cells (ATCC No. CCL-92.1.) known in the art as a cultured preadipocyte cell line so that the changes in gene expression at the earliest stage of differentiation might be analyzed. As a result, nearly 100 clones were obtained as genes of which the adipocyte differentiation-promoting protein expression increases within 12 hours from the start of adipocyte differentiation induction and which are activated within 12 hours from the start of adipocyte differentiation induction. From among the clones, a polynucleotide having the base sequence shown under SEQ ID NO:1 was obtained as a gene especially outstanding in expression. The base sequence of the polynucleotide as shown under SEQ ID NO:1 was determined using a cDNA expressed in the early stage of murine adipocyte differentiation, namely before adipocyte differentiation induction and after 3 hours of induction. The polynucleotide is designated as murine clone 24 nucleotide.

Thus, the polynucleotide of the invention is a polynucleotide encoding a protein having a function to promote adipocyte differentiation and having a property such that it is activated within 12 hours from the start of adipocyte differentiation induction.

In this specification, "activation" means expression or acceleration of expression.

Polynucleotides containing a base sequence homologous to the base sequence shown under SEQ ID NO:1, or polynucleotides complementary to such polynucleotides were looked up in BLAST, whereupon the sequence of a Chinese hamster-derived mRNA for which no function is described at all and which has been registered under the accession number AF371372 with full length of 2794 bp was hit upon. The homology between the base sequence shown under SEQ ID NO:1 and the base sequence of the Chinese hamster-derived mRNA is 88.12%, and the homology between the portion from the initiation codon to termination codon (bases Nos. 100 to 2520 in SEQ ID NO:1) in base sequence shown under SEQ ID NO:1 and the known sequence of the Chinese hamster ORF (open reading frame) is 91.72%.

The polynucleotide of the invention is a polynucleotide having a base sequence identical or at least 93%, 95% or 98% homologous to the base sequence shown under SEQ ID NO:1 or a polynucleotide complementary to said polynucleotide; it is a polynucleotide which encodes an adipocyte differentiation-promoting protein capable of being activated within 12 hours from the start of adipocyte differentiation induction and is activated within 12 hours from the start of adipocyte differentiation induction.

Further, the polynucleotide of the invention is a polynucleotide containing a base sequence identical or at least 93%, 95% or 98% homologous to the base sequence from base No. 100 to base No. 2520 of the base sequence shown under SEQ ID NO: 1 or a polynucleotide complementary to said polynucleotide; it is a polynucleotide encoding a protein capable of being activated within 12 hours after the start of adipocyte differentiation induction and having a function to promote adipocyte differentiation.

A human polynucleotide having a novel base sequence was determined by human homolog cloning based on the murine polynucleotide having the base sequence shown under SEQ ID NO:1. The novel base sequence is shown under SEQ ID NO:9.

Thus, the human polynucleotide of the invention is a polynucleotide containing the base sequence shown under SEQ ID NO:9 or a polynucleotide complementary to said polynucleotide; it is a polynucleotide encoding a protein having a function to promote adipocyte differentiation and capable of being activated within 12 hours from the start of adipocyte differentiation induction; for example, it is a cDNA. Said polynucleotide is referred to as human clone 24 nucleotide.

Further, the human polynucleotide of the invention is a polynucleotide containing bases Nos. 26 to 2425 of the base sequence shown under SEQ ID NO:9 or a polynucleotide complementary to said polynucleotide; it is a polynucleotide which encodes a protein having a function to promote adipocyte differentiation and has a property such that it is activated within 12 hours from the start of adipocyte differentiation induction.

The homology between the murine clone 24 polynucloetide shown under SEQ ID NO:1 and the human clone 24 polynucloetide shown under SEQ ID NO:9 is 2089/2444 (mouse vs human), namely 85.47%.

The homology between the sequence of the Chinese hamster-derived mRNA and that of the human polynucleotide is 87.36%, and the homology between the sequence from the initiation codon to termination codon (from base No. 26 to base No. 2425) in the human polynucleotide having the base sequence shown under SEQ ID NO:9 and the known sequence of the Chinese hamster ORF is 87.53%.

From the viewpoint of SEQ ID NO:9 and in view of the homology to the known Chinese hamster ORF sequence (87.36%), the polynucloetide of the invention includes nucleotides containing a base sequence identical or at least 89%, 91% or 93% homologous to the base sequence shown under SEQ ID NO:9 or polynucleotides complementary to said polynucleotides.

In view of the homology between the sequence from the initiation codon to termination codon (base No. 26 to base No. 2425 in the base sequence) in the human polynucleotide and the known Chinese hamster ORF sequence (87.53%), the polynucleotide of the invention includes polynucleotides containing a base sequence identical or at least 89%, 91% or 93% homologous to the sequence from base No. 26 to base No. 2425 of the base sequence shown under SEQ ID NO:9 or polynucleotides complementary to said polynucleotides.

The above-mentioned polynucleotides of the invention can each be extracted from murine cells, human cells or other animal cells within 12 hours, in particular at about 6 hours, from the start of adipocyte differentiation induction. The polynucleotides of the invention can also be obtained from genomic DNA, cell/tissue-derived cDNA, a cell/tissue-derived cDNA library, or synthetic DNA. The "polynucleotide" of the invention is either DNA or RNA.

The term "clone" simply so referred to herein sometimes means the clone 24 nucleotide or clone 24 polynucleotide.

The protein of the invention is a protein capable of being activated within 12 hours, in particular at about 6 hours, from the start of adipocyte differentiation induction and is a protein promoting adipocyte differentiation.

The protein of the invention is preferably a protein containing an amino acid sequence at least 96%, 98% or 100% homologous to the protein amino acid sequence shown under SEQ ID NO:2 over the full length thereof. More preferably, the protein of the invention is the gene translation product of a polynucleotide containing a base sequence at least 96%, 98% or 100% homologous to the base sequence shown under SEQ ID NO:1 over the sequence from base No. 100 to base No. 2520 thereof.

As the protein containing an amino acid sequence 100% homologous to the amino acid sequence of the protein specified under SEQ ID NO:2, there may be mentioned a protein capable of being activated in the early stage of murine adipocyte differentiation. This protein is designated as murine clone 24 protein.

Further, the human protein of the invention includes a protein containing the amino acid sequence shown under SEQ ID NO:10. The human protein of the invention is the product of gene translation of a polynucleotide containing the sequence from base No. 26 to base No. 2425 in the polynucleotide base sequence shown under SEQ ID NO:9. From the SEQ ID NO:10 viewpoint, the invention includes a protein, including salts thereof, containing an amino acid sequence at least 93%, 95% or 97% homologous to the amino acid sequence shown under SEQ ID NO: 10 over the full length thereof.

The protein shown under SEQ ID NO:10 is a protein capable of being activated within 12 hours, in particular at about 6 hours, from the start of human adipocyte differentiation induction and is a protein promoting adipocyte differentiation. This protein is designated as human clone 24 protein.

The polynucleotide of the invention is involved in the expression of PPARγ, C/EBPα, C/EBPδ and SREBP-1, which are proteins expressed after the lapse of 12 hours from the start of adipocyte differentiation induction, and is closely related to the expression of PPARγ, in particular. Presumably, the protein of the invention directly or indirectly acts on such transcription factors as the PPAR family, C/EBP family, and SREBP-1/ADD1. There is the possibility of its stimulating other pathways as well.

The polynucleotide of the invention or the protein or peptide of the invention which is produced as a gene translation product of the polynucleotide is useful in the treatment or diagnosis of a lifestyle-related disease selected from among obesity, hypertension, hyperlipidemia, diabetes, and heart diseases or cerebral apoplexy resulting from arteriosclerosis, etc.

Sequence Homology

The reason why the language "identical or at least 93% homologous to a base sequence", for instance, is used in describing the homology aspect of the invention is that since the homology between the Chinese hamster-derived mRNA registered under the accession number AF371372 with a length of 2794 bp as found in BLAST and the base sequence shown under SEQ ID NO:1 is 88.12% and the homology between the sequence from the initiation codon to termination codon shown under SEQ ID NO:1 (base No. 100 to base No. 2520 in the base sequence) and the known Chinese hamster ORF sequence is 91.72%, the sequence of said mRNA is to be excluded.

The reason why the language "at least 80% homologous to a base sequence over the full length thereof" is used in describing another aspect of the invention is that the homology on the amino acid level between mouse and human has already been reported to be 84% [Y. Zhang et al., Nature, vol. 372, page 425 (1994); JP-A No. H08-333394]. It has been revealed that the group of genes involved in lifestyle-related diseases such as hypertension, diabetes and obesity retains 80% or higher homology among animals (JP-A No. H11-75865). Therefore, it is reasonable to consider that as regards the polynucleotide of the invention and the protein of the invention as well, the homology among human and other primates and rabbit and other rodents, for instance, will be 80% or higher based on the sequences disclosed herein. The reasonability of the above estimation is supported by the fact that the homology between the murine clone 24 polynucleotide shown under SEQ ID NO:1 and the human clone 24 polynucleotide shown under SEQ ID NO:9 is 85.47%.

Cloning of the Polynucleotide of the Invention

As for the means of cloning a polynucleotide encoding the protein of the invention, it can be amplified by the PCR method using synthetic DNA primers each having a part of the base sequence of the protein of the invention, or it can be selected by hybridization using labeled DNA fragment or synthetic DNA encoding a part or the whole region of the protein of the invention against an appropriate vector containing DNA insert, for instance. The hybridization can be carried out by the method described in Molecular Cloning, 2nd edition (J. Sambrook et al., Cold Spring Harbor Lab. Press, 1989), for instance. In cases where a commercial library is used, it can be carried out according to the procedure described in the manual attached thereto. According to the intended purpose thereof, the cloned protein-encoding DNA can be used either as such or, after digestion with a restriction enzyme where desired or after addition of a linker. The DNA may have ATG as the translation initiation codon on the 5' terminal end and may have TAA, TGA or TAG as the translation termination codon on the 3' terminal end. It is also possible to add these translation initiation codon and translation termination codon using appropriate synthetic DNA adaptors.

Vector etc. for the Expression of the Polynucleotide

The vector of the invention is a recombinant vector containing a polynucleotide identical or at least 93% homologous to the polynucleotide shown under SEQ ID NO:1 or a polynucleotide complementary to said polynucleotide and preferably is a recombinant vector containing a polynucleotide containing the base sequence from base No. 100 to base No. 2520 in the base sequence shown under SEQ ID NO:1.

Further, the vector of the invention which contains a polynucleotide involved in human adipocyte differentiation is a recombinant vector containing a polynucleotide containing the base sequence shown under SEQ ID NO:9 or a polynucleotide complementary to said polynucleotide and preferably is a recombinant vector containing a polynucleotide containing the base sequence from base No. 26 to base No. 2425 in the base sequence shown under SEQ ID NO:9 or a polynucleotide complementary to said polynucleotide.

The vector having the polynucleotide sequence of the invention can be constructed in the conventional manner. The vector suited for such purpose has a promoter region upstream of the insertion site of the polynucleotide of the invention. This promoter may be a known one and can be selected according to the host cell. In cases where *Escherichia coli* or a like bacterial species is used as the host, the lac promoter, trp promoter, T7 promoter, tac promoter, or λPL promoter, for instance, can be utilized. When a yeast is used as the host, the GADPH promoter, ADH promoter, PGK promoter, and PH05 promoter can be utilzed. When animal-derived cells are used as the host, there may be mentioned the human cytomegalovirus promoter, SV40 virus-derived promoter, EF-1 α promoter, β actin promoter, and metallothionein promoter. Preferably, the vector for the expression of the polynucleotide according to the invention has a transcription termination signal downstream from the site of insertion of the polynucleotide of the invention. Furthermore, it is desirable that the vector contains a marker for identification, for example a drug resistance marker.

Host

As for the host that can be used in the practice of the invention, bacteria of the genus *Escherichia*, bacteria of the genus *Bacillus*, yeasts, insect cells, insects, animal cells and so forth are suitable.

As typical examples of the bacteria of the genus *Escherichia*, *Escherichia coli* JM109 [ATCC 53323, product of Toyobo Co., Ltd.], JM103 [Nucleic Acids Research, vol. 9, 309 (1981), K12•DH1 [Proc. Natl. Acad. Sci. USA, vol. 60, 160 (1968), JA221 [Journal of Molecular Biology, vol. 120, 517 (1978)], HB11 [Journal of Molecular Biology, vol. 41, 459 (1969)], and C600 [Genetics, vol. 39, 440 (1954)], among others are mentioned.

As the bacteria of the genus *Bacillus*, among others, *Bacillus subtilis* M1114 [Gene, vol. 24, 255 (1983)], and 207-21 [Journal of Biochemistry, vol. 95, 87 (1984)] are mentioned.

As the yeasts, *Saccharomyces cerevisiae* AH22, AH22R-, NA87-11A, DKD-5D, 20B-12, *Schizosaccharomyces pombe* NCYC1913, NCYC2036, and *Saccharomyces pichiapastoris*, among others are mentioned.

As for the insect cells, when the virus is AcNPV, cabbage armyworm larva-derived established cell line cells (*Spodoptera frugiperda* cells; Sf cells), *Trichoplusia ni* mesenteron-derived MG1 cells, *Trichoplusia ni* egg-derived High Five™ cells, *Mamestra brassicae*-derived cells, and

*Estigmena acrea*-derived cells are mentioned. When the virus is BmNPV, silkworm-derived established cell line cells (*Bombyx mori* N cells; BmN cells), among others are mentioned. As the above Sf cells, for example, Sf9 cells (ATCC CRL1711), and Sf21 cells (for both, Vaughn, J. L. et al., In Vivo, vol. 13, 213-217 (1977)) are mentioned.

As the insects, silkworm larvae [Maeda et al., Nature, vol. 315, 592 (1985)] is mentioned, for instance.

Usable as the animal cells are, for example, monkey COS-7, Vero, Chinese hamster cells CHO (hereinafter referred to as CHO cells for short), dhfr gene-deficient Chinese hamster cells CHO [abbreviation: CHO(dhfr–) cells], mouse L cells, mouse AtT-20, murine myeloma cells, rat GH3, human FL cells.

Transformant Production

The transformant of the invention is derived from the above-mentioned host by allowing it to harbor the recombinant vector mentioned above.

Bacteria of the genus *Escherichia* can be transformed according to the method described in Proc. Natl. Acad. Sci. USA, vol. 69, 2110 (1972), or Gene, vol. 17, 107 (1982), for instance.

Bacteria of the genus *Bacillus* can be transformed according to the method described in Molecular and General Genetics, vol. 168, 111 (1979), for instance.

Yeasts can be transformed according to the method described in Methods in Enzymology, vol. 194, 182-187 (1991), or Proc. Natl. Acad. Sci. USA, vol. 75, 1929 (1978), for instance.

Insect cells or insects can be transformed according to the method described in Bio/Technology, vol. 6, 47-55 (1988), for instance.

Animal cells can be transformed according to the method described in Saibo Kogaku (Cell Engineering), Supplement No. 8, Saibo Kogaku Jikken Purotokoru (Protocols for Cell Engineering Experiments), 263-267 (1995) (published by Shujunsha), or Virology, vol. 52, 456 (1973), for instance.

Transformant Cultivation

The transformant of the invention can be cultured under conditions sufficient for protein formation with the conditions mentioned below being taken into consideration and, as a result, the desired protein can be recovered from the culture medium or transformant.

When the host is a bacterial strain of the genus *Escherichia* or *Bacillus*, the transformant is preferably cultured in a liquid medium, which contains carbon sources, nitrogen sources, inorganic substances and other factors necessary for the growth of the transformant. As the carbon sources, there may be mentioned glucose, dextrin, soluble starch, and sucrose, among others. As the nitrogen sources, there may be mentioned ammonium salts, nitrate salts, corn steep liquor, peptone, casein, meat extracts, soybean meal, potato extracts and like inorganic or organic substances. As the inorganic substances, there may be mentioned calcium chloride, sodium dihydrogen phosphate, and magnesium chloride, among others. Yeasts, vitamins, growth promoting factors and the like may be added to the medium. The medium desirably has a pH of about 5 to 8.

In culturing bacteria of the genus *Escherichia*, M9 medium containing glucose and casamino acids (Miller, Journal of Experiments in Molecular Genetics, 431-433, Cold Spring Harbor Laboratory, New York, 1972) is preferably used. If necessary, such an agent as 3-indolylacrylic acid, for instance, may be added thereto for effective promoter functioning. In cases where the host is a bacterial strain of the genus *Escherichia*, the cultivation is generally carried out at about 15-43° C. for about 3-24 hours. If necessary, aeration and/or agitation can be made.

In cases where the host is a bacterial strain of the genus *Bacillus*, the cultivation is generally carried out at about 30-40° C. for about 6 to 24 hours. If necessary, aeration and/or agitation can be performed. When the host is a yeast, the transformant is cultured, for example, in Burkholder minimal medium [Bostian, K. L. et al., Proc. Natl. Acad. Sci. USA, vol. 77, 4504 (1980)] or SD medium containing 0.5% of casamino acids [Bitter, G. A. et al., Proc. Natl. Acad. Sci. USA, vol. 81, 5330 (1984)]. The medium is preferably adjusted to a pH of about 5 to 8. The cultivation is generally carried out at about 20° C.-35° C. for about 24-72 hours, if necessary with aeration and/or agitation.

In culturing a transformant derived from an insect cell host or insect host, Grace's insect medium (Grace, T. C. C., Nature, vol. 195, 788 (1962)) adequately supplemented with 10% inactivated bovine serum and/or some other additive or additives is used as the medium, among others. The pH of the medium is preferably adjusted to about 6.2 to 6.4. The cultivation is generally carried out at about 27° C. for about 3-5 days, if necessary with aeration and/or agitation.

In culturing a transformant derived from an animal cell host, MEM medium [Science, vol. 122, 501 (1955)], DMEM medium 5 [Virology, vol. 8, 396 (1959)], RPMI 1640 medium [Journal of the American Medical Association, vol. 199, 519 (1967)], or 199 medium [Proceedings of the Society for the Biological Medicine, vol. 73, 1 (1950)] containing about 5-20% of fetal bovine serum, for instance, is used as the medium. The pH is preferably about 6 to 8. The cultivation is generally carried out at about 30° C.-40° C. for about 15-60 hours, if necessary with aeration and/or agitation. In the above manner, the protein of the invention can be formed in the transformant cells.

Protein Formation in a Cell-Free System

In addition to the protein production by transformant cultivation as mentioned above, it is also possible to form the desired protein using a cell-free cultivation system such as a high-efficiency cell-free protein synthesis system of Invitrotech or Roche's in vitro translation/transcription system, for instance.

Protein Isolation and Purification

The protein of the invention can be isolated and purified, for example, by the method mentioned below. In extracting the protein of the invention from cultured bacterial cells or other cells, a method comprising collecting bacterial cells or other cells after culturing in the conventional manner, suspending them in an appropriate buffer, disrupting them by sonication, lysozyme treatment and/or freezing and thawing, and recovering a crude protein-containing extract by centrifugation or filtration, for instance, or a similar method is adequately used. The buffer solution may contain a protein denaturing agent, such as urea or guanidine hydrochloride, or a detergent such as Triton X-100 (trademark, product of Union Carbide). Usable as such known method of isolation/purification are such solubility-based methods as salting out and solvent precipitation, such methods mainly based on molecular weight differences as dialysis, ultrafiltration, gel filtration and SDS-polyacrylamide gel electrophoresis, such charge difference-based methods as ion exchange chromatography, such specific affinity-based methods as affinity chromatography, such hydrophobicity difference-based methods as reversed phase high performance liquid chromatography, and such isoelectric point difference-based methods as isoelectric focusing, among others.

In cases where the protein obtained by such a method as mentioned above is in a free form, it can be converted to a salt form by a known method or a method based thereon. Conversely, when it is obtained in a salt form, it can be converted to a free form or another salt form by a known method or a method based thereon. It is also possible to arbitrarily modify the protein produced by the recombinant or partially deprive a polypeptide from the protein by causing an appropriate protein-modifying enzyme to act thereon before purification or after purification. Usable as the protein-modifying enzyme are, for example, trypsin, chymotrypsin, arginine endopeptidase, protein kinase, and glycosidase. The presence of the thus-formed protein of the invention or a salt thereof can be confirmed by a labeled ligand binding assay or an enzyme immunoassay using a specific antibody.

Human Homolog Cloning

It is possible to find out a highly homologous sequence and predict the full length of the human homolog by homology search against NCBI Genome Sequencing (Human Genome Database), using the murine full-length DNA sequence shown under SEQ ID NO: 1 as determined in the manner mentioned above, which is a polynucleotide capable of being activated within 12 hours from the start of adipocyte differentiation induction. The RT-PCR method, for instance, can be applied to human homolog cloning. The full length of the human homolog predicted as above and actually sequenced by the RT-PCR method is the base sequence shown under SEQ ID NO:9. From the full length base sequence of the human homolog as shown under SEQ ID NO:9, it can be predicted that said base sequence is a gene encoding a protein composed of 800 amino acid residues and that the amino acid sequence of said protein is as shown under SEQ ID NO:10.

Method of Antagonist and Agonist Identification

The method of identifying a compound antagonizing or agonizing the protein of the invention comprises the following steps (a) and (b).

(a) The step of bringing a candidate compound into contact with cells in which the protein of the invention is being expressed or cells responsive to the protein of the invention;
(b) The step of observing as to binding, or stimulation or inhibition as a functional response; or the step of comparing the cells that have been contacted with the candidate compound with the cells of the same kind that have not been contacted with the candidate compound with respect to an ability associated with an activity of the protein of the invention.

The antagonist or agonist of the invention can be identified by the above method of identification.

Method of Polynucleotide Detection; Diagnosis Based on the Polynucleotide

A disease in a subject to be diagnosed which is associated with the activation of the protein of the invention in the subject, or the sensitivity to such disease can be diagnosed in the following manner. The diagnosis is performed by determining as to whether there is a mutation in the base sequence encoding the protein of the invention in the genome of the subject to be diagnosed or not; and/or analyzing the occurrence or amount of the protein of the invention in a sample derived from the subject.

For detecting or assaying the polynucleotide of the invention, primers comprising not less than 8 consecutive bases but not more than 100 consecutive bases selected from the base sequence of the polynucleotide of the invention are synthesized and, separately, mRNA is extracted from cells or blood, for instance, and amplified by the RT-PCR method while converting mRNA to DNA, or the target polynucleotide is amplified by the T7-based mRNA amplification method (Van Gelder, R. N. et al., Proc. Natl. Acad. Sci. USA, 87: 1663-1667, 1990). The thus-amplified polynucleotide can be detected by any of various electrophoretic techniques. It is also possible to add Cy3-dUTP or Cy5-dUTP in the step of polynucleotide amplification for fluorescent labeling of the amplified polynucleotide and detect the labeled polynucleotide using a DNA microarray (Brown, P. O. et al.: Nature Genet., 21, sup.: 33-37, 1999).

For assaying the mRNA extracted, the quantitative PCR method using a fluorescent dye is carried out [Yodosha (publisher): non-RI Jikken no Saishin Purotokoru (Latest Protocols for non-RI Experiments), edited by Kurihara et al., 1999, pp. 83-89]. This method reveals the extent of occurrence of the mRNA in cells. Based on that extent of expression thereof, the condition of obesity can be checked.

It is also possible to detect and measure a plurality of polynucleotides simultaneously using a DNA microarray. For example, by reacting the labeled polynucleotide prepared from a sample with a plurality of polynucleotides including the polynucleotide of the invention as bound onto a substrate, it becomes possible, in the manner mentioned above, to judge which polynucleotide on the substrate is reactive with the labeled polynucleotide and as to whether there is any reactive polynucleotide or not. This judgment makes it possible to understand the condition of some or other lifestyle-related disease and utilize the findings in the treatment thereof. Further, by allowing a plurality of obesity-related polynucleotides, including of the polynucleotide of the invention, to be bound to a substrate, it becomes possible to understand the condition and extent of obesity by the same technique and utilize the findings in the treatment thereof.

As regards the detection of the polynucleotide of the invention, it is also possible to detect the same by capillary electrophoresis utilizing Applied Biosystem's ABI PRISM 310, PRISM 3100 or PRISM 3700.

It has been revealed that single nucleotide polymorphisms (hereinafter, SNPs) resulting from substitution of some or other base for a specific nucleic acid base in a polynucleotide and resulting in modification in activity of a protein as a gene product, modification in the ability of the protein of the invention to bind to a receptor thereof, modification in reactivity of said protein with a drug, modification in the stability of said protein, or suspension of the synthesis of said protein, are very important. As for the polynucleotide of the invention as well, the significance of detecting such SNPs is very important.

If a high-density SNP marker gene map for the adipocyte differentiation-related polynucleotides of the invention become available, might make it easy to make comparisons between healthy subjects and patients based on SNPs that can specify the genes causative of diabetes. If such a high-density SNP map is used, it will become possible to perform a correlation analysis (whole genome association study) using a large size of non-family-related samples. Through substitution of one base, in particular, SNPs result in changes in the corresponding amino acid, which changes in turn lead to changes in physical properties of the protein proper. On the enzyme level, for instance, a decrease or increase in enzyme activity as resulting from the change of an amino acid in the vicinity of the active center and, on the receptor level, a decrease or increase in binding ability as resulting from the change of an amino acid in the vicinity of the acceptor center. The adjustment of the dose of a drug and/or the selection of a different drug according to the gene polymorphism of each individual subject is referred to tailored medicine, for instance.

Applicable as the method of detecting SNPs in the polynucleotides of the invention are, for example, the method of using U.S. Nanogen's nanochips (Gilles et al., Nature Biotechnology, 365-370, 17, 1999), the method comprising polynucleotide sequence determination, the method using DNA chips or DNA arrays, the method using a mass spectrometer (Legler et al., Transfusion, 36:426-431, 1996), the method using primer extensions, the Luminex method (Iannone et al., Cytometry, 39:131-140, 2000), etc.

As the diagnostic agent to be constituted for detecting each of the polynucleotides mentioned above, there may be mentioned a diagnostic agent comprising a polynucleotide having a sequence comprising at least 10 consecutive bases taken out of those polynucleotides containing a base sequence identical or at least 80% homologous to the base sequence shown under SEQ ID NO:1 or those polynucleotides complementary to said polynucleotides.

Further, the diagnostic agent may comprise a polynucleotide having a sequence comprising at least 10 consecutive bases taken out of those polynucleotides containing a base sequence identical or at least 80% homologous to the sequence from base No. 100 to base No 2520 in the base sequence shown under SEQ ID NO:1 or those polynucleotides complementary to said polynucleotides. The diagnostic agent constituted for human polynucleotide detection, in particular, is a diagnostic agent comprising a polynucleotide having a base sequence comprising at least 10 consecutive bases taken out of those polynucleotides containing the base sequence shown under SEQ ID NO:9 or those polynucleotides complementary to said polynucleotides.

More preferably, the diagnostic agent constituted for human polynucleotide detection is a diagnostic agent comprising a polynucleotide having a sequence comprising at least 10 consecutive bases taken out of those polynucleotides containing the base sequence from base No. 26 to base No. 2425 in the base sequence shown under SEQ ID NO:9 or those polynucleotides complementary to said polynucleotides.

Detection of the Protein or Peptide, Detection of an Antibody to the Protein or Peptide, and Application to Diagnosis For detecting the protein of the invention, the immunoassay method is generally used. For example, mice, rats, rabbits, goats, swine, cows and bulls, sheep, chickens or like animals can be immunized, for antibody production, with the protein shown under SEQ ID NO:2 or SEQ ID NO:10 or a peptide having an amino acid sequence composed of three or more consecutive amino acid residues as contained in either of the sequences. In carrying out this immunization, it is a general practice to add a substance called adjuvant. Usable as the adjuvant are Freund's complete adjuvant, Freund's incomplete adjuvant, alum, and various other known adjuvants. In the case of immunizing mice, the spleen of each immunized mouse is excised after a certain period of immunization, and the splenocytes, which are antibody-producing cells, are fused to myeloma cells, and hybridomas producing an antibody specifically binding to the protein shown under SEQ ID NO:2 are prepared by carrying out cloning.

An antibody produced upon cultivation of such a hybridoma is purified by various methods, and the antibody obtained is immobilized on a solid phase. Separately, the antibody is labeled with an enzyme, fluorescent dye, metal colloid, latex, DNA or RNA, for instance, to give a labeled antibody. The above immobilized antibody and labeled antibody are reacted with a sample such as cells, blood or one of the fractions thereof, and the presence or absence or the amount of the label bound to the solid phase is checked or assayed, whereby the protein of the invention in the sample can be quantitated.

Since the protein of the invention is specifically found in adipocytes, the quantitation thereof makes it possible to understand the extent and condition of obesity.

For assaying the protein of the invention contained in samples, an antibody is prepared by immunizing rabbits, rats, sheep or goats with that protein or a partial peptide of that protein as an antigen (in this case, the preparation of a monoclonal antibody capable of binding to a specific recognition site being included). The thus-obtained antibody is allowed to be physically adsorbed on such a material as polystyrene, a latex or nitrocellulose, or biotin is introduced into the antibody in advance and the biotinylated antibody is reacted with streptavidin, avidin or the like bound in advance to a solid phase for the preparation of a solid phase, or an antibody-bound solid phase is prepared by covalently binding the antibody to a solid phase via a carboxyl, amino, sulfhydryl or like group occurring on the solid phase. The thus-obtained antibody-bound solid phase is reacted with a sample, such as cells, blood or any of the fractions thereof for binding the antigen contained in the sample to the solid phase and, then, the antigen bound to the antibody-bound solid phase is reacted with a labeled antibody derived from the antibody prepared by the above-mentioned process by binding thereto a radioisotope, enzyme, fluorescent dye or nucleic acid or biotin or a like label. The steps of reacting the antibody-bound solid phase with the sample and with the labeled antibody can also be carried out simultaneously. By assaying the label thus bound to the solid phase, it is possible to assay the protein of investigation contained in the sample.

A different method such as mentioned below can also be used as the method of antibody detection. Thus, the protein of the invention or a partial peptide of that protein is used as an antigen and immobilized on a solid phase to give an antigen-bound solid phase. Then, the antigen-bound solid phase is reacted with a substance obtained by labeling the antigen and a sample such as cells, blood or any of the fractions thereof, and the label bound is quantitated, whereby the antibody amount contained in the sample can be assayed. Therefore, a diagnostic agent capable of detecting an antibody immunologically specific to the protein of the invention can be constructed.

While the reaction systems described above all comprises the antigen or antibody directly immobilized on a solid phase, a reaction system comprising an oligonucleotide bound to a solid phase and an antigen or antibody bound to an oligonucleotide complementary to that oligonucleotide as bound to the solid phase, as disclosed in U.S. Pat. No. 5,789,165, is also applicable. Furthermore, as described in JP-A No. H10-253632 or EP 0905517 A1, it also becomes possible to detect or assay different items simultaneously. For example, it presumably becomes possible to simultaneously detect markers associated with lifestyle-related diseases such as diabetes, hypertension and obesity and judge the level of such lifestyle-related diseases depending on the degrees of detection of respective proteins. Further, it presumably becomes possible to detect and assay such markers as obesity-related proteins or peptides simultaneously, and understand the state of obesity and utilize the findings in the treatment of obesity.

For immunologically detecting the protein of the invention or an antibody to that protein, there may be mentioned, in addition to the methods described above, the method involving immunoagglutination (JP-A No. H06-3358), the surface plasmon resonance (SPR) method using BIAcore of Biacore International AB (Sweden), for instance, and the method using a crystal oscillator (JP-A No. 1109-292397), among others.

As the diagnostic agent constituted for detecting the above-mentioned protein of the invention, there may be mentioned a diagnostic agent comprising the protein of the invention or a salt thereof. In a preferred embodiment, the diagnostic agent of the invention is a diagnostic agent comprising a protein or peptide comprising at least 5 consecutive amino acid residues out of the protein of the invention or a salt thereof. Another diagnostic agent for detecting the protein of the invention comprises an antibody to the protein of the invention.

Use for Therapeutic Purposes

The present invention provides a method of therapeutic treatment of those abnormal conditions such as lifestyle-related diseases, including obesity, hypertension, hyperlipidemia, diabetes, renal diseases, insulin tolerance, lipodystrophy, CNS diseases, and/or heart diseases or cerebral apoplexy resulting from arteriosclerosis, which are related to the activity of an excessive or insufficient amount of the protein of the invention or a peptide constituting a part of that protein. In cases where the activity of the protein of the invention or a peptide constituting a part of that protein is excessive, several methods can be used.

One measure is characterized in that a pharmaceutical composition comprising an effective amount of the above-mentioned inhibitor compound (antagonist) in combination with a pharmaceutically acceptable carrier is administered to a subject to be treated to thereby block the ligand binding to the protein or peptide of the invention or inhibit the second signal and inhibit the activation so that the abnormal condition may be improved.

Another measure is characterized in that a pharmaceutical composition comprising a therapeutically effective amount of a compound capable of activating the polynucleotide of the invention (i.e. agonist) in combination with a pharmaceutically acceptable carrier is administered so that the abnormal condition may be improved.

In another approach, the protein or peptide of the invention or a salt thereof in a soluble form, which is capable of binding to a ligand in competition with the protein or peptide of the invention, may be administered. Typical examples of such competitor substance include the protein of the invention and peptides constituting a part of that protein. Thus, the pharmaceutical composition of the invention may be a pharmaceutical composition comprising said protein or a salt thereof, or a peptide composed of at least 5 consecutive amino acid residues of said protein or a salt thereof.

According to a further technique, which utilizes the expression blocking method, the polynucleotide of the invention or a polynucleotide complementary to that polynucleotide may be administered to inhibit the gene activation.

Such pharmaceutical composition of the invention is a pharmaceutical composition comprising a polynucleotide having a base sequence identical or at least 80% homologous to the base sequence of the clone 24 polynucleotide as shown under SEQ ID NO:1, or a polynucleotide complementary to that polynucleotide.

Preferably, it is a pharmaceutical composition comprising a polynucleotide having a base sequence comprising at least 10 consecutive bases taken out of those polynucleotides containing a base sequence identical or at least 80% homologous to the base sequence shown under SEQ ID NO:1 or those polynucleotides complementary to said polynucleotides and, more preferably, it is a pharmaceutical composition comprising a polynucleotide having a base sequence comprising at least 10 consecutive bases taken out of those polynucleotides containing a base sequence identical or at least 80% homologous to the sequence from base No. 100 to base No. 2520 in the base sequence shown under SEQ ID NO:1 or to those polynucleotides complementary to said polynucleotides.

As regards the human clone 24 polynucleotide, in particular, polynucleotides containing the base sequence shown under SEQ ID NO:9 or polynucleotides complementary to those polynucleotides are taken into consideration. Preferred is a pharmaceutical composition comprising a polynucleotide having a base sequence comprising at least 10 consecutive bases taken out of those polynucleotides containing the base sequence shown under SEQ ID NO:9 or those polynucleotides complementary to said polynucleotides. More preferred is a pharmaceutical composition comprising a polynucleotide having a base sequence comprising at least 10 consecutive bases taken out of those polynucleotides containing the sequence from base No. 26 to base No. 2425 in the base sequence shown under SEQ ID NO:9 or to those polynucleotides complementary to said polynucleotides.

These pharmaceutical compositions utilize, as a therapeutic agent, an antisense to a sequence around ATG. In these pharmaceutical compositions, an antisense sequence formed within cells or separately administered can be utilized in the conventional manner. Refer, for example, to Oligodeoxynucleotides as Antisense Inhibitors of Gene Expression, CRC Press, Boca Raton, Fla. (1988), and O'Connor, J. Neurochem. (1991) 56: 560. As an alternative, a triple helix-forming oligonucleotide may be provided together with the gene. Cf. e.g. Lee et al., Nucleic Acids Res. (1979) 6: 3073; Cooney et al., Science (1988) 241: 456; Dervan et al., Science (1991) 251: 1360. These oligomers themselves may be administered as such, or related oligomers may be activated invivo.

As an alternative, the formation of the polynucleotide of the invention in cells of a subject to be treated may be made effective by means of gene therapy. For example, the polynucleotide of the invention may be treated, as mentioned above, and inserted into a replicative defective retrovirus vector for activation thereof. Then, the retrovirus expression construct is isolated and introduced into packaging cells transduced with a retrovirus plasmid vector containing the RNA encoding the protein of the invention and, then, the packaging cells are allowed to form infective viral particles containing the desired polynucleotide. These producer cells may be administered to a subject to be treated for invivo treatment of the cells and invivo activation of the protein. Applicable to the gene therapy are the methods described in Human Molecular Genetics, T. Strachan and A. P. Read, BIOS Scientific Publishers Ltd. (1996), Chapter 20, Gene Therapy and other Molecular Genetic-based Therapeutic Approaches (and references cited therein).

A pharmaceutical composition can be prepared by incorporating an antibody to the clone 24 protein or human clone 24 protein of the invention or to a peptide comprising a part of the amino acid sequence constituting either of the proteins.

In cases where such antibody is administered, it can be expected that the adipocyte differentiation activity may be reduced.

Formulation and Administration

In the treatment of a subject to be treated who requires enhanced activation of the protein of the invention, a therapeutically effective amount of a protein containing an amino acid sequence identical or at least 80% homologous to the whole length of the protein of the invention as shown under SEQ ID NO:2, or a peptide constituting a part of that protein, or a salt thereof, an antibody to the protein or a peptide constituting a part of the protein, an agonist, an antagonist peptide, or a size-reduced molecule derived therefrom, each in a soluble form, may be administered to a subject to be treated.

Such formulation comprises a therapeutically effective amount of the above-mentioned substance or a salt thereof, and a pharmaceutically acceptable carrier or excipient. Such carrier includes, but is not limited to, saline, buffered saline, dextrose, water, glycerol, ethanol, and mixtures of these. The formulation should be adequate for the route of administration, as is well known to those skilled in the art. The present invention is further concerned with a pharmaceutical pack or kit comprising one or more containers with one or more of the above-mentioned active ingredients of the invention contained therein.

The protein and other compounds of the invention may be used singly or in combination with some other compounds such as therapeutic compounds. A preferred form of systemic administration of the pharmaceutical composition includes injection, typically intravenous injection. Other routes of injection, such as hypodermic, intramuscular or intraperitoneal, may also be used. Another means for systemic administration includes administration through a mucous membrane or percutaneous administration using a penetrant such as a bile acid salt or fusidic acid or some other surfactant. If a satisfactory formulation which melts in the entrails or capsule formulation is available, oral administration is also possible. These compounds may be administered locally, and they may be in the form of plasters or ointments, pastes, gels, etc.

The necessary dose range depends on the peptide, route of administration, nature of formulation, nature of symptom of the subject to be treated, and judgment of the doctor in charge. An appropriate dose is within the range of 0.1 to 100 µg per kilogram of body weight of the subject to be treated. Considering the differences in efficacy among the various compounds to be used and among various routes of administration, however, the necessary dose range is estimated to be wide. For example, higher doses are estimably required in oral administration than in intravenous injection. The doses can be varied using standard and routine experiments for optimization, as well understood in the relevant field of art.

In the above-mentioned method of treatment, which is frequently referred to as "gene therapy", it is also possible to cause the protein of the invention, which is to be used for the treatment, to be formed in a subject to be treated. Therefore, for example, cells derived from the subject to be treated may be treated exvivo using a retrovirus plasmid vector and a polynucleotide such as a protein-encoding DNA or RNA. The cells treated are then introduced into the subject to be treated.

EXAMPLE 1

Confirmation of Differentiation into Adipocytes

Figure 1:
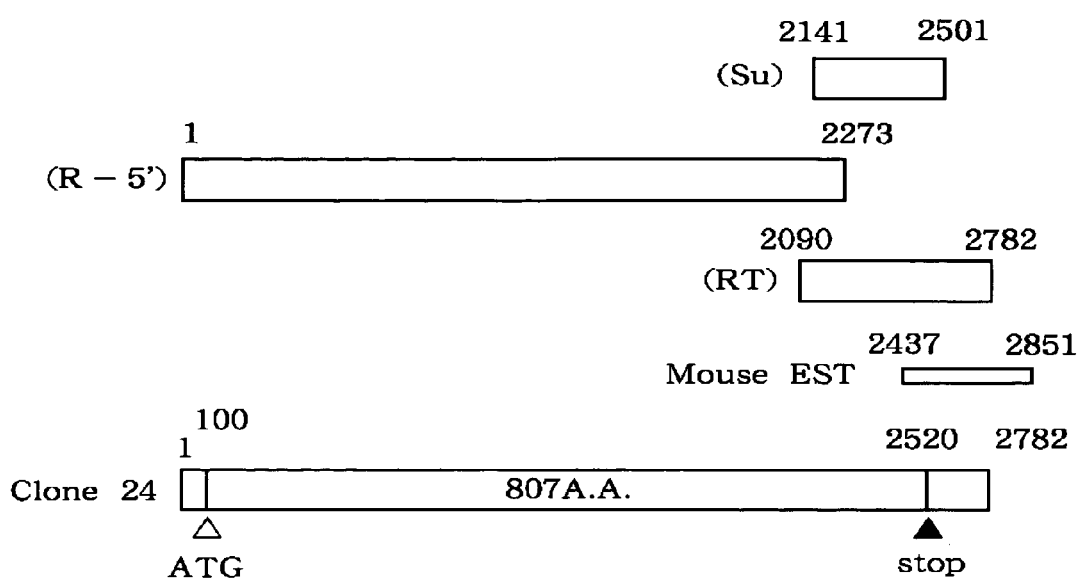
FIG. 1 shows a schematic representation of the clone 24 mouse cDNA and further illustrates the subcloning for base sequence determination of the clone 24 based on the information about the DNA fragment Su obtained by the subtraction technique.

Murine 3T3-L1 cells (ATCC No. CCL-92.1.) capable of differentiating into adipocytes were cultured in a collagen type I dish (product of FALCON) using a basal medium (DMEM, 4 µg/ml KM, 10% calf serum) in 5% $CO_2$ at 37° C. After the lapse of 2 days after arrival of cells at a confluent state, when cells were in the resting phase, the medium was replaced with a differentiation inducing medium (DMEM, 40 µg/ml KM, 10% FBS, 0.5 mM 1-methyl-3-isobutylxanthine (Mix), 10 µg/ml insulin, 1 µM dexamethasone (Dex)), cultivation was carried out under these differentiation conditions for 48 hours, and the medium was replaced with a differentiation promoting medium (DMEM, 40 µg/ml KM, 10% FBS, 5 µg/ml insulin). Medium change was carried out with the differentiation promoting medium at 2-day intervals. It was confirmed that murine 3T3-L1 cells (ATCC No. CCL-92.1) began to contain small fat drops at around the 4th day and thereon and, after one week, had differentiated into mature adipocytes.

EXAMPLE 2

Preparation of mRNA

Using TRIzol (product of GIBCO BRL) and according to the manual attached to TRIzol (product of GIBCO BRL), the whole amount of RNA of the murine 3T3-L1 cell origin was prepared from murine 3T3-L1 cells (ATCC No. CCL-92.1.) before adipocyte differentiation induction or at 3 hours after the start of differentiation induction. mRNA before adipocyte differentiation induction and mRNA at 3 hours after adipocyte differentiation induction were prepared from the respective whole amounts of RNA using Oligotex-dT 30 (product of Daiichi Pure Chemicals).

EXAMPLE 3

Activity Measurement at 3 Hours from Adipocyte Differentiation Induction by the PCR-Select cDNA Subtraction Method The following steps i) to vii) were carried out using the known PCR select cDNA subtraction kit (product of CLONTECH Laboratories).

i) Synthesis of Tester cDNA and Driver cDNA

The murine 3T3-L1 cell (ATCC No. CCL-92.1.)-derived mRNA before adipocyte differentiation induction as prepared in Example 2 was used as the driver mRNA, and the mRNA prepared in Example 2 at 3 hours after adipocyte differentiation induction was used as the tester mRNA. Single-stranded cDNAs were synthesized from the driver mRNA and tester mRNA and, then, a double-stranded driver cDNA and a double-stranded tester cDNA were synthesized.

ii) Double-stranded cDNA Cleavage with the Restriction Enzyme RsaI

The double-stranded driver cDNA and tester cDNA obtained in the above step i) were each cleaved with the restriction enzyme RsaI, and blunt-ended fragments were prepared.

iii) Adapter Ligation

The tester cDNA obtained in the above step ii) was divided into two groups. Adaptor 1 was ligated to one group, and adaptor 2 was ligated to the other group.

iv) First Hybridization

The two kinds of the tester cDNAs obtained by adapter ligation in the above step iii) were separately subjected to hybridization with an excessive amount of the driver cDNA.

v) Second Hybridization

Further, an excessive amount of the driver cDNA was mixed with the two kinds of the tester cDNAs resulting from hybridization with the driver cDNA as obtained in the above step iv), and hybridization was carried out.

vi) First PCR

The hybridized tester cDNA obtained in the above step iv) was amplified by the PCR method using a primer common to the two adapter sites.

vii) Second PCR

Finally, the DNA was amplified using two primers specific to the two adapter sites.

The tester cDNA hybridized with the driver cDNA was not amplified. On the other hand, the tester-specific polynucleotide (gene), namely the polynucleotide showing an increased degree of activation after 3 hours of differentiation induction, alone was amplified.

EXAMPLE 4

PCR Product Subcloning and Clone 24 Plasmid

The clone 24 murine cDNA is schematically shown in FIG. 1. The amplified polynucleotide-containing reaction mixture after carrying out the second PCR as obtained by the subtraction method in Example 3 was subjected to phenol extraction, followed by CIAA extraction and EtOH precipitation. The DNA pellet obtained was dissolved in 17 µl of sterilized water, and adapter cleavage was effected using 10 units of RsaI at 37° C. overnight under the conditions: 10 mM Tris-HCl (pH 7.5), 10 mM $MgCl_2$, 1 mM DTT. After 0.7% agarose gel electrophoresis and purification using DB81 (product of Whatman), the DNA fragment Su (cf. FIG. 1) was obtained.

Based on the information about the DNA fragment Su, primers were designed, and 5'-RACE was carried out. As a result, a band of about 2 Kbp was obtained. This was recovered and designated as nucleotide R-5' (cf. FIG. 1). The nucleotide R-5' was subcloned in T vector (pBluescript KS+) and sequenced using DSQ-1000 (product of Shimadzu Corp.). On the other hand, data base retrieval using the 3' side sequence of the clone 24 revealed an identical base sequence registered in EST and, referring to this base sequence, primers were designed and RT-PCR was carried out. As a result, a band of about 700 bp was obtained. This was recovered and designated as nucleotide RT (cf. FIG. 1). The nucleotide RT was subcloned in T vector (pBluescript KS+) and sequenced using DSQ-1000 (product of Shimadzu Corp.). Thus was obtained a 2782 bp clone polynucleotide corresponding to the full length of the murine 3T3-L1 cell (ATCC No. CCL-92.1.)-derived clone 24 cDNA. This polynucleotide is designated as clone 24 polynucleotide.

The 100th base-involving ATG was estimated as the translation initiation codon. As a result, the clone 24 was estimated as a gene encoding 807 amino acid residues. Using the base sequence of the clone 24 as determined and the amino acid sequence deduced from the base sequence, homology search was carried out in the database BLAST, and it was revealed that there is a Chinese hamster-derived mRNA of which no function is described at all and which has been registered under the accession number AF371372 with a length of 2794 bp. Since the homology between the base sequence shown under SEQ ID NO:1 and the base sequence of the Chinese hamster-derived mRNA is 88.12% and the homology between the sequence from the initiation codon to the termination codon (base No. 100 to base No. 2520 in the base sequence) in the base sequence shown under SEQ ID NO:1 and the known Chinese hamster-derived ORF is 91.72%, the clone 24 polynucleotide is considered to be a novel gene.

50 ng of a 5' terminally dephosphorylated pBluescript KS+/EcoRV vector and 150 ng of the DNA fragment were subjected to ligation reaction. Competent cells of *Escherichia coli* JM109 [ATCC 53323, product of Toyobo] were transformed with 1.2 µl of the ligation reaction mixture by the heat shock method, and a subcloned clone 24 plasmid was obtained. The transformant produced in this Example 4 has been deposited with the National Institute of Advanced Industrial Science and Technology International Patent Organism Depositary, which is an international depository institution, under the accession number FERM BP-7803. Originally, the transformant was deposited with the international depository institution on Nov. 29, 2000 (original date of deposition) under the accession number FERM P-18131 and, on Nov. 16, 2001, the original deposit was transferred to the deposit under the Budapest Treaty.

EXAMPLE 5

Base Sequence and Amino Acid Sequence Determination

The base sequence of the clone 24 polynucleotide was determined using ABI PRISM 310 (product of Perkin-Elmer) and DSQ 1000 (product of Shimadzu). The thus-revealed base sequence of the clone 24 polynucleotide is shown under SEQ ID NO:1. It was found that the clone 24 polypeptide is composed of 2782 bases. Deduction of the amino acid sequence from the codon sequence of the clone 24 polynucleotide indicates that the polynucleotide encodes the clone 24 protein composed of 807 amino acid residues. The amino acid sequence of the clone 24 protein is shown under SEQ ID NO:2.

EXAMPLE 6

Comparisons with Existing Base Sequences and Amino Acid Sequences

For the base sequence of the clone 24 polynucleotide and the amino acid sequence of the clone 24 protein, homology search was carried out in the databases Genbank, EMBL, EST and Swiss Prot.

As a result of FASTA and BLASTN, the clone 24 polynucleotide shows no homology to the polynucleotides registered with their respective functions and thus was found to be a novel substance as a polynucleotide specifically activated on the occasion of differentiation of preadipocytes into adipocytes.

As a result of BLASTNP, the amino acid sequence of the clone 24 protein has no homology to the registered proteins with respective known functions, hence was found to be a novel substance as a protein specifically activated on the occasion of differentiation of preadipocytes into adipocytes.

EXAMPLE 7

Insert Recovery and Probe Preparation

The plasmid of the subcloned clone 24 obtained in Example 4 was prepared by the alkali SDS method described in Molecular Cloning, this plasmid was cleaved with the restriction enzymes XbaI and HindIII and subjected to 1.0% agarose gel electrophoresis, and the band corresponding to the insert was recovered using DE81 (product of Whatman). 50 to 100 ng of the DNA fragment was labeled with [$\alpha$-$^{32}$P]dCTP (product of Amersham Pharmacia Biotech) using the BcaBEST™ Labeling Kit (product of TaKaRa) to give a labeled probe. The labeled probe obtained through a column of Sephadex G-50 (product of Amersham Pharmacia Biotech). A $^{32}$P-labeled probe was thus prepared.

EXAMPLE 8

Northern Blot Analysis

A 25-µg portion of each of the total RNAs respectively prepared from murine 3T3-L1 cells (ATCC No. CCL-92.1.) before adipocyte differentiation induction (0 hour) and after 0.5, 1, 3, 6, 12 and 24 hours after the start of differentiation induction was subjected to electrophoresis on a 1% modified gel (2% formaldehyde, 1×Mops, 1% agarose). The gel was treated with 50 mM NaOH for 25 minutes (alkali denaturation) and then with 200 mM NaOAc (pH 4.0) for 40 minutes (neutralization), and the RNA was transferred to HybondN+ (product of Amersham Pharmacia Biotech). The transfer was carried out for 12 hours or longer. The buffer used was 20×SSC. After transfer, the filter was treated with 50 mM NaOH for 5 minutes, washed with 2×SSC, and dried at 80° C. for 2 hours, followed by UV irradiation for fixation.

Using a hybridization buffer (5×SSPE, 50% formaldehyde, 5× Denhardt's, 0.1% SDS, 20 µg/ml salmon sperm DNA), prehybridization was carried out overnight at 42° C. The hybridization buffer was replaced with a fresh portion, the thermally denatured probe was added, and hybridization was carried out at 42° C. overnight. The filter was then washed with a primary washing solution (2×SSPE, 0.1% SDS) at room temperature for 10 minutes, further with the primary washing solution at 55-65° C. for 15 minutes, then with a secondary washing solution (1×SSPE, 0.1% SDS) at 65° C. for 15 minutes, and finally with a tertiary washing solution (0.5×SSPE, 0.1% SDS) at 65° C. for 10 minutes, and then subjected to autoradiography. The results obtained are shown in FIG. 2.

Figure 2:
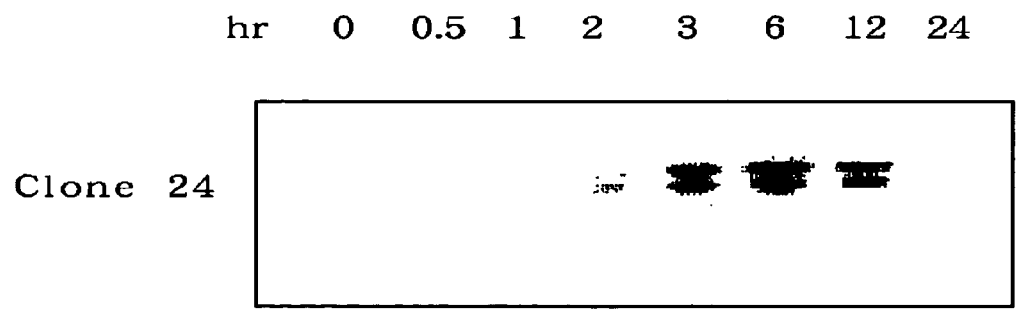
FIG. 2 is an autoradiogram showing that a labeled probe prepared from the clone 24 reacts with mRNA samples prepared from cells from 3 hours to 12 hours after the start of differentiation induction, with a peak at 6 hours after the start of differentiation induction.

The autoradiogram shown in FIG. 2 revealed that the labeled probe prepared from the clone 24 polynucleotide does not react with the mRNA prepared from the cells before the start of adipocyte differentiation induction (0 hour) but reacts with the mRNA prepared from the cells at 3 hours to 12 hours. Thus, it was found that the sequence cloned in the clone 24 polynucleotide is a sequence specifically activated in adipocyte differentiation.

EXAMPLE 9

Identification of the Site of Localization of mRNA i) Plasmid Construction

The full length of the clone 24 polynucleotide shown under SEQ ID NO:1 was amplified by RT-PCR and, after recovery and purification, the amplification product was subcloned in the GFP expression vector pEGFP (product of Clontech).

ii) Plasmid Purification

The above subcloned plasmid was subjected to two repetitions of ultracentrifugation by the Triton lysis method using cesium chloride. The supercoil plasmid DNA was thus purified.

iii) Transfection

Figure 3:
FIG. 3(c) is a photomicrograph of the GFP of the clone 24 expressed in a cell.
FIG. 3(a) is a photomicrograph of the whole cell as a control.
FIG. 3(b) is a photomicrograph of the nucleus in the cytoplasm as stained by the DAPI method.
Figure 3:
Figure 3:
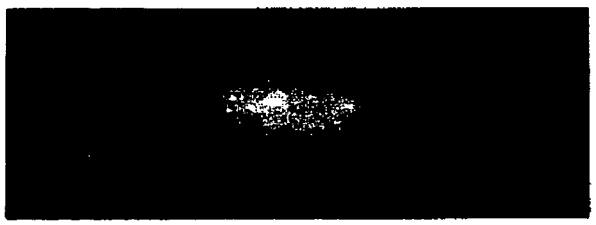

Murine NIH/3T3 clone 5611 cells (product of JCRB 0615) which had lost the function to differentiate into adipocytes were transfected with the supercoil plasmid DNA obtained in the above step by the lipofectamine (product of GIBCO BRL) method. After 2 days, the transfected cells were washed three times with PBS(−). Then, the cells were fixed by 30 minutes of treatment with 3 ml of PBS(−) containing 4% paraformaldehyde contained in a dish with a diameter of 6 cm. Then, the cells were washed twice with PBS and, after washing, they were checked for the expression of GFP under a fluorescent microscope (BX-50, product of OLYMPUS). FIG. 3(c) is a photomicrograph showing the GFP expressed in a cell in the above step. FIG. 3(a) is a photomicrograph of the whole cell as a control. FIG. 3(b) is a photomicrograph of the nucleus in the cytoplasm as stained alone by the DAPI method.

Figure 4:
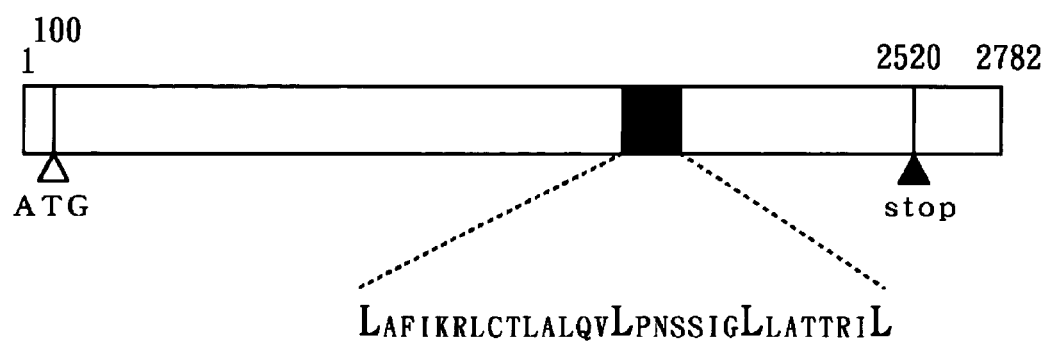
FIG. 4 is a schematic representation of the clone 24 polypeptide. In the sequence, the sequence site considered to be a leucine zipper structure is shown in detail.

Upon comparison of the photographs (a) to (c), it is evident that the clone 24 protein-encoding mRNA occurs only in the nucleus. As to whether the amino acid sequence of the clone 24 protein as estimated from the clone 24 polynucleotide forms a leucine zipper structure or not, comparison with other proteins having a leucine zipper structure, namely c-fos, C/EBPα, CREB and Jun B, indicates that they are common in that the leucine-to-leucine distance is 7 bases or 14 bases, hence it is estimated that also the clone 24 protein has a leucine zipper structure. That the clone 24 protein-encoding mRNA is present only in the nucleus is presumably due to the formation of a dimer via the leucine zipper structure and its functioning as a transcription factor in the nucleus. FIG. 4 is a schematic representation of the clone 24 polypeptide. In the sequence, the sequence site considered to be a leucine zipper structure is shown in detail.

EXAMPLE 10

Production of an NIH/3T3 Cell Line Showing Excessive Clone 24 Expression i) Plasmid Construction The sequence from No. 87 bp to No. 2636 bp in the base sequence of the clone 24 was amplified by RT-PCR using Ampli-Taq Gold (product of Perkin-Elmer) with an oligonucleotide having the base sequence shown below under SEQ ID NO:11 as a upper layer primer and an oligonucleotide having the sequence shown below under SEQ ID NO:12 as a lower layer primer. After 0.8% agarose gel electrophoresis, the amplification product was recovered and purified using DE81 (product of Whatman) and subcloned in T vector (pBluescript SK+). For transformation, the *Escherichia coli* DH5α strain was used. After confirmation of the base sequence using DSQ-1000 (product of Shimadzu), the base sequence was cleaved with the restriction enzymes BamHI and XhoI, and the fragment was recovered and purified and subcloned in pDON-AI (product of TaKaRa) at the BamHI, SalI.

SEQ ID NO:11
CGC AGG CCT AAG GAT GAA GGC G

SEQ ID NO:12
CAG GGT CTT CTG TGG CCC TGC TCC ii) Plasmid Preparation

Plasmid preparation was carried out using CONCERT (registered trademark of GIBCO BRL) High Purity Plasmid Midiprep Systems (product of GIBCO BRL) and according to the manual attached thereto.

iii) Cultivation of PT67 Packaging Cells

Cultivation of PT67 packaging cells was carried out in high-glucose Dulbecco's modified Eagle medium (product of GIBCO BRL) containing 10% FBS under 5% $CO_2$ at 37° C.

iv) Transfection and Viral Solution Recovery

On the day before transfection, $7.0 \times 10^5$ PT-67 cells were sowed per 10-cm plate. On the day of transfection, transfection was carried out with 14 μg of pDON-AI (TaKaRa) with the full-length clone 24 inserted therein or pDON-AI containing no insert by the calcium phosphate method. At 72 hours after transfection, each cell culture supernatant was recovered as a viral solution.

v) Cultivation of Target Cells NIH/3T3

Cultivation was carried out in Dulbecco's modified Eagle medium (product of Nissui Pharmaceutical Co.) under 5% $CO_2$ at 37° C.

vi) Viral Infection and Single Cell Line Cloning

On the day before infection, $5.0 \times 10^5$ target NIH/3T3 cells were sowed per 10-cm plate. On the day of infection, a culture fluid containing 5 ml of the viral solution prepared together with 8 μg/ml of polybrene (product of SIGMA) was added to the target NIH/3T3 cells. At 24 hours after infection, the cells were diluted stepwise at ratios 1/4, 1/10, 1/100 and 1/1000 and cultured in a medium containing 0.5 mg/ml of G418 (product of Nakalai Tesque) for about 10 days, and a G418-resistance cell line, namely cells with the target gene integrated into the chromosome thereof, namely an NIT/3T3 cell line showing excessive clone 24 expression, was obtained.

EXAMPLE 11

Confirmation of Clone 24 Expression in Cells Produced i) Total RNA Recovery

The total RNA was recovered from each of the NIH/3T3 cells showing excessive clone 24 expression as obtained in Example 10 and control NIH/3T3 cells transfected with the blank vector according to the manual attached to TRIzol (product of GIBCO BRL).

ii) Probe Preparation

The pBluescript SK+ clone 24 was cleaved with the restriction enzyme PstI and, after 0.8% agarose electrophoresis, a 1.2 kbp band corresponding to the clone 24 cDNA was purified. The DNA fragment corresponding to 60 ng was labeled with $[\alpha-^{32}P]dCTP$ (product of Amersham Pharmacia Biotech) using BcaBEST (registered trademark of TaKaRa) Labeling kit (product of TaKaRa) to give a probe.

iii) Northern Blot Analysis

The total RNA recovered (10 μg) was subjected to 1% modified gel (2% formaldehyde, 1×MOPS, 1% agarose) electrophoresis. The gel was treated with 50 mM NaOH for 25 minutes (alkali denaturation) and then with 200 mM NaOAc (pH 4.0) for 40 minutes (neutralization treatment), and the RNA was transferred to Hybond N+ (trademark, product of Amersham Pharmacia Biotech). The transfer was carried out for 12 hours or longer. The buffer used was 20×SSC. After transfer, the filter was treated with 50 mM NaOH for 5 minutes, washed with 2×SSC, dried at 80° C. for 2 hours, and subjected to UV irradiation for fixation.

Figure 5:
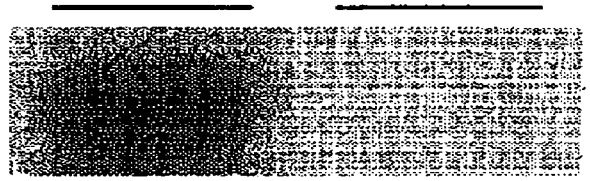
FIG. 5 shows an autoradiogram of NIH/3T3 cells showing ectopic expression of the clone 24.

Using a hybridization buffer (5×SSPE, 50% formaldehyde, 5× Denhardt's, 0.1% SDS, 20 μg/ml salmon sperm DNA), prehybridization was carried out overnight at 42° C. The hybridization buffer was replaced with a fresh portion, the thermally denatured probe was added, and hybridization was carried out at 42° C. overnight. The filter was then washed with a primary washing solution (2×SSPE, 0.1% SDS) at 42° C. for 15 minutes and further with a fresh portion of the washing solution at 65° C. for 15 minutes, and then subjected to autoradiography. The autoradiogram obtained is shown in FIG. 5.

This result revealed that the clone 24 mRNA derived from the plasmid constructed in Example 10 i) is expressed in the NIH/3T3 cell line showing excessive clone 24 expression as prepared in Example 10.

EXAMPLE 12

Figure 7:
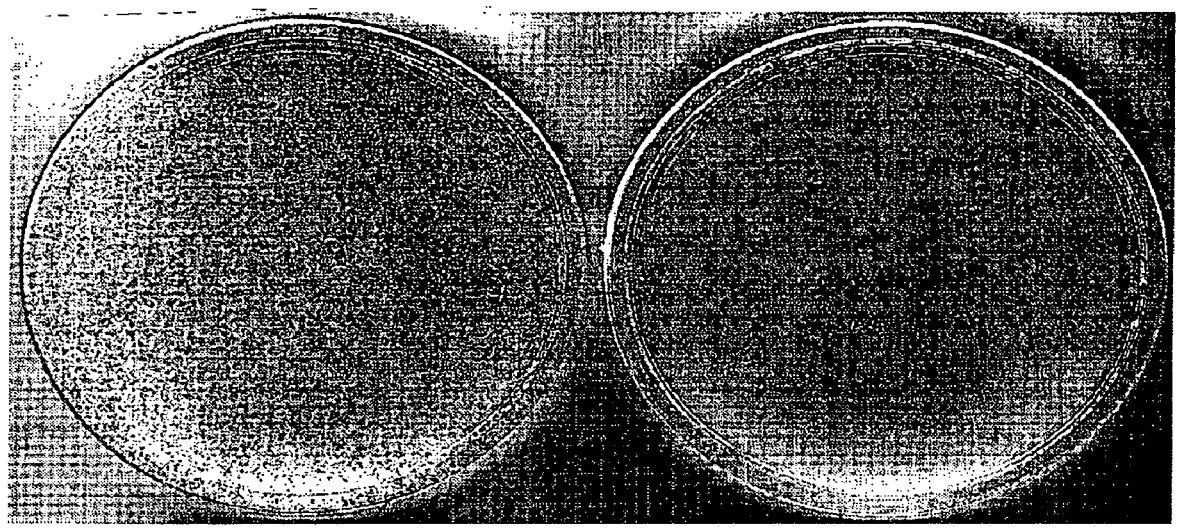
FIG. 7 shows the results of Oil-Red-O staining of NIH/3T3 cells showing ectopic expression of the clone 24 on day 8 after differentiation induction and of control cells.

Differentiation of NIH/3T3 Cells Showing Excessive Clone 24 Expression into Adipocytes i) Differentiation Induction The clone 24 over expressed NIH/3T3 cells obtained in Example 10 were cultured in a collagen type I dish (product of FALCON) using Dulbecco's modified Eagle medium (product of Nissui Pharmaceutical) containing 10% calf serum under 5% $CO_2$ at 37° C. After the lapse of 2 days after arrival of cells at a confluent state, when cells were in the resting phase, the medium was replaced with a differentiation inducing medium [DMEM, 10% FBS, 0.5 mM 1-methyl-3-isobutylxanthine (MIX), 10 μg/ml insulin, 1 μM dexamethasone (DEX), BRL 49653 (product of Smithkline Beecham Pharmaceutical)], cultivation was carried out under these conditions for 48 hours, and the medium was replaced with a differentiation promoting medium (DMEM, 10% FBS, 5 μg/ml insulin, BRL 49653). Medium exchange was carried out with the differentiation promoting medium at 2-day intervals, and cultivation was continued to day 8.

ii) Oil-Red-O Staining 5 ml of ice-cooled 4% paraformaldehyde/PBS(-) was added to the cells on the 8th day after differentiation induction without removing the culture medium, and the mixture was allowed to stand at room temperature for 20 minutes. The medium was removed, 5 ml of ice-cooled 4% paraformaldehyde/PBS(-) was added, and the mixture was allowed to stand at room temperature for 1 hour. After washing with three portions of distilled water, 5 ml of an Oil-Red-O staining solution (0.5% Oil-Red-O, 60% 2-propanol) was added, and the mixture was allowed to stand at room temperature for 1 hour. The plate was washed with three portions of distilled water and then air-dried. The stained plate is shown in FIG. 7. Upon observation under a microscope, accumulation of fatty drops was confirmed in the excessive clone 24 expression NIH/3T3 cells while no fatty drops were observed in the control cells. Thus, differentiation into adipocytes was confirmed.

EXAMPLE 13

Human Homolog Cloning i) Estimation of the Sequence of the Human Homolog Using NCBI Genome Sequencing (Human Genome Database)

For the full-length clone 24 murine polynucleotide sequence determined in Example 7, homology searching was carried out in NCBI Genome Sequencing BLAST the Human genome, and a highly homologous sequence was found out on chromosome 10. When an initial methionine codon-containing exon was regarded as the first exon, the sequence was constituted of 21 exons in total. Since the gt-ag rule was preserved among all exons and introns, the full-length sequence of the human homolog could be anticipated.

ii) HeLa Cell Cultivation

Human homolog cloning was carried out by RT-PCR. HeLa cells were used as the template. For HeLa cell cultivation, MEM (trademark, product of Nissui Pharmaceutical) supplemented with 10% FBS (trademark, product of Dainippon Pharmaceutical) was used.

iii) Total RNA Recovery

The total RNA was recovered from the HeLa cells cultured to a confluent state using TRIzol (product of GIBCO BRL) and according to the manual attached thereto.

iv) Human Homolog Cloning by Reverse Transcriptase Coupled Polymerase Chain Reaction (RT-PCR)

Based on the full-length sequence anticipated in the above step i), oligonucleotides having the base sequences shown below under SEQ ID NO:3 to 8 were used in combination as primers, and RT-PCR was carried out using the RT-PCR mixture composition given below. The cDNA template was prepared from the whole RNA of HeLa cells prepared in the above steps ii) and iii) using ReverTra Dash (product of Toyobo) and according to the manual attached thereto.

```
SEQ ID NO:3 (upper layer): 5'-GCC GGC ATT CAT TTA AGG CC-3'

SEQ ID NO:4 (lower layer): 5'-CTT CGC ATG AAC AGG CTC AC-3'

SEQ ID NO:5 (upper layer): 5'-CAG ATC CCA AGC TTT CGC-3'

SEQ ID NO:6 (lower layer): 5'-AGC AAA CTT GGC AAG ACC-3'

SEQ ID NO:7 (upper layer): 5'-AAG AAG GCC CAG AGG TCA-3'

SEQ ID NO:8 (lower layer): 5'-GTC CAC TGA CTT CAT TCC-3'
```

RT-PCR Mixture Composition:
2 µl 10×PCR buffer for KOD-Plus-
2 µl 12 mM dNTPs
0.8 µl 25 mM MgSO₄
2 µl cDNA template
1.2 µl upper layer and lower layer primers (each 10 mM)
11.6 µl sterile H₂O
0.4 µl KOD-Plus-DNA polymerase (1.0 U/µl)

The primer combinations mentioned above were SEQ ID NO: 3/SEQ ID NO:4, SEQ ID NO:5/SEQ ID NO:6, and SEQ ID NO:7/SEQ ID NO:8, and the RT-PCR conditions were as follows: one cycle: 2 minutes at 94° C. 30 cycles: 15 seconds at 94° C. 30 seconds at 60° C., and 2 minutes at 68° C.

v) RT-PCR Fragment Purification and Base Sequence Determination

The PCR reaction products were separated by 0.7% agarose gel electrophoresis and then recovered and purified using DE81 (product of Whatman). Each DNA fragment was subcloned in pBluescript KS+ and sequenced using DSQ-1000 (product of Shimadzu). The reaction product obtained with SEQ ID NO:3/SEQ ID NO:4 was not subcloned but sequenced using Gene Rapid (product of Amersham Pharmacia Biotech).

vi) Full-Length Sequence Determination of Clone 24 Human Homolog

Figure 6:
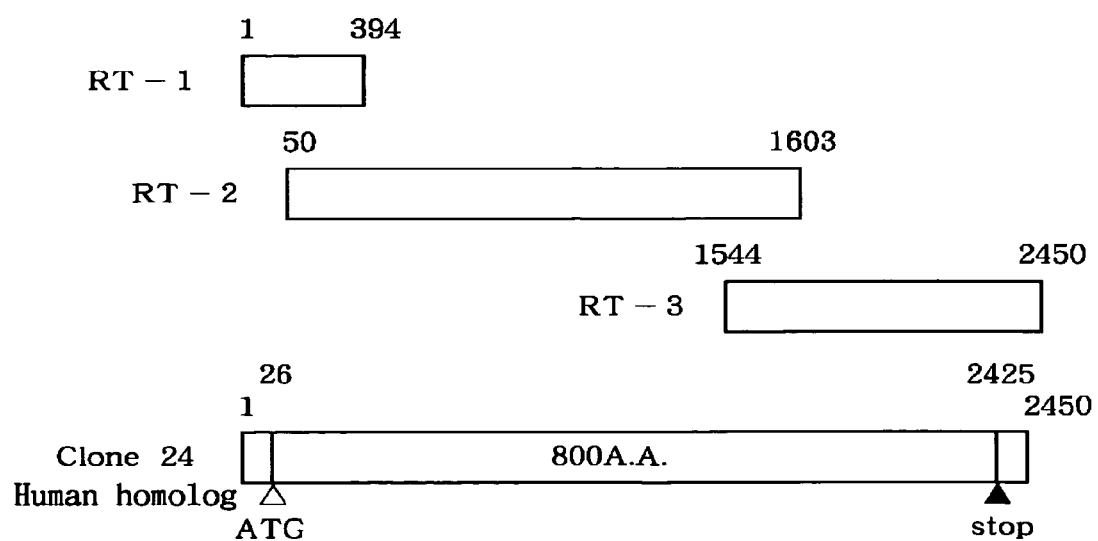
FIG. 6 schematically shows the clone 24 human homolog cDNA.

The clone 24 human homolog cDNA is schematically shown in FIG. 6. The 394 bp band detected following RT-PCR with the combination SEQ ID NO:3/SEQ ID NO:4 was sequenced, and the band was designated as RT-1. It was revealed that the sequence in this region is 100% identical to the sequence anticipated in the above step i).

The 1554 bp band detected following RT-PCR with the combination SEQ ID NO:5/SEQ ID NO:6 was sequenced, and the band was designated as RT-2. The homology to the anticipated sequence was 1553/1554, namely 99.94%.

The 907 bp band detected following RT-PCR with the combination SEQ ID NO:7/SEQ ID NO:8 was sequenced, and the band was designated as RT-3. It was revealed that the sequence in this region is 100% identical to the sequence anticipated in the above step i).

The full-length nucleic acid sequence of the clone 24 human homolog polynucleotide cloned in the above manner is shown under SEQ ID NO:9.

The homology between the murine clone 24 polynucleotide shown under SEQ ID NO:2 and the human homolog shown under SEQ ID NO:9 was 2089/2444=85.47%.

In the clone 24 human homolog polynucleotide, the 26th base-containing ATG corresponding to the amino acid presumed as the first methionine in the murine clone 24 was regarded as the translation initiation codon. As a result, it is estimated that the clone 24 human homolog polynucleotide be a gene encoding a protein composed of 800 amino acid residues and that the amino acid sequence of that protein be as shown under SEQ ID NO:10.

EXAMPLE 14

Identification of Antibodies to the Clone 24 i) Introducing Maleimide Group into KLH 0.1 M sodium phosphate buffer (pH 7.0) containing 5 mg of Keyhole limpet hemocyanin (trademark, product of Calbiochem, hereinafter referred to as KLH) was reacted with 1 mg of EMCS (trademark, product of Dojin Chemical) at 37° C. for 1 hour and, then, the unreacted EMCS was removed using PD10 (trademark, product of Amersham Pharmacia Biotech) equilibrated with 0.1 M phosphate buffer (pH 6.0) to give maleimidated KLH.

ii) Preparation of PEPTIDE 4-Coupled KLH 2 mg of the maleimidated KLH obtained in the above step i) was reacted with 1 mg of Cys Lys Asp Ile Thr Pro Ser Tyr Lys Ile Arg Pro Leu Thr Glu Ala Glu Lys (SEQ ID NO:14), which is a product of terminally introducing Cys into the sequence Lys Asp Ile Thr Pro Ser Tyr Lys Ile Arg Pro Leu Thr Glu Ala Glu Lys (SEQ ID NO:13, hereinafter referred to as PEPTIDE 4), which is in turn the sequence composed of 17 amino acids, i.e. from the 266th to 282nd amino acid, in the murine clone 24 protein shown under SEQ ID NO:2, at 37° C. for 1 hour, and the unreacted peptide was removed by dialysis to give PEPTIDE 4-coupled KLH.

iii) Preparation of PEPTIDE 8-Coupled KLH 2 mg of maleimidated KLH was reacted with 1 mg of Cys Leu Arg Ile Lys Glu Val Glu Val Lys Lys Asp Thr Glu Asp Ile Asn Lys Pro Lys Arg Phe (SEQ ID NO:16), which is a product of terminally introducing Cys into the sequence Leu Arg Ile Lys Glu Val Glu Val Lys Lys Asp Thr Glu Asp Ile Asn Lys Pro Lys Arg Phe (SEQ ID NO:15, hereinafter referred to as PEPTIDE 8), which is in turn the sequence composed of 21 amino acids, i.e. from the 426th to 446th amino acid, in the murine clone 24 protein shown under SEQ ID NO:2, at 37° C. for 1 hour, and the unreacted peptide was removed by dialysis to give PEPTIDE 8-coupled KLH.

iv) Preparation of PEPTIDE 10-Coupled KLH 2 mg of maleimidated KLH was reacted with 1 mg of Cys Glu Ser Ser His Ser Lys Arg Lys Asp Lys Phe Leu Pro Gly Asp Ser (SEQ ID NO:18), which is a product of terminally introducing Cys into the sequence Glu Ser Ser His Ser Lys Arg Lys Asp Lys Phe Leu Pro Gly Asp Ser (SEQ ID NO:17, hereinafter referred to as PEPTIDE 10), which is in turn the sequence composed of 16 amino acids, i.e. from the 750th to 765th amino acid, in the murine clone 24 protein shown under SEQ ID NO:2, at 37° C. for 1 hour, and the unreacted peptide was removed by dialysis to give PEPTIDE 10-coupled KLH.

v) Rabbit Immunization

The PEPTIDE 4-coupled KLH, PEPTIDE 8-coupled KLH and PEPTIDE 10-coupled KLH (each 50 µg) were respectively mixed with Freund's complete adjuvant to give emulsions, which were administered to rabbits dorsally subcutaneously for immunization. After the lapse of one month from this immunization, booster immunization was performed using the same emulsions and, one week later, blood was sampled from each rabbit.

vi) Preparation of Blocked, Peptide-Immobilized Solid Phase Modules

Figure 8:
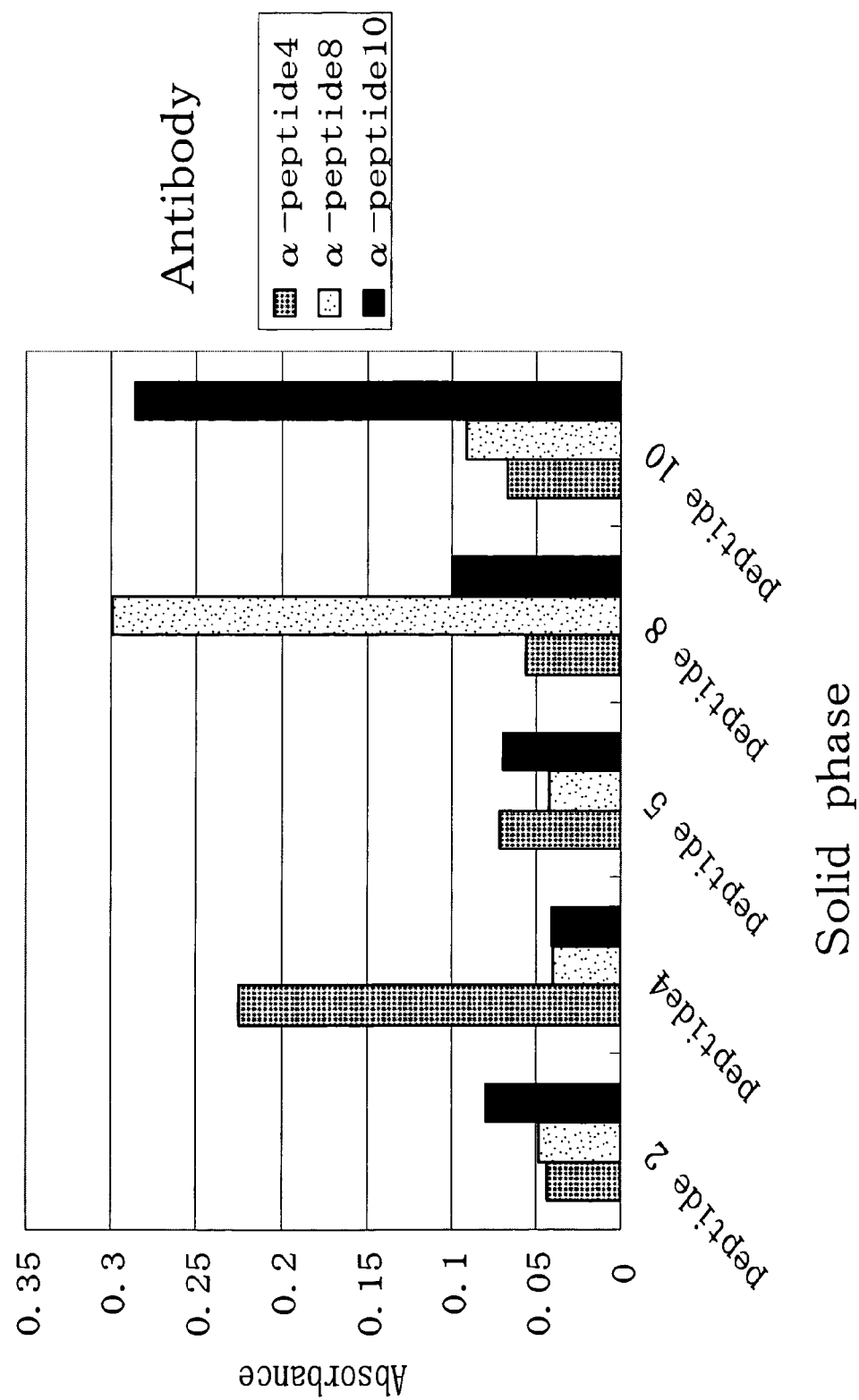
FIG. 8 is a graphic representation of the results of identifying antibodies to the clone 24, which results indicate that the antibodies obtained by immunization with PEPTIDE 4, PEPTIDE 8 and PEPTIDE 10, which are partial peptides constituting the clone 24 protein, react with a solid module carrying the respective peptides immobilized thereon.

Peptide solutions were prepared by diluting, to 10 g/ml, the above-mentioned clone 24 protein-derived peptides, namely PEPTIDE 4, PEPTIDE 8 and PEPTIDE 10, and two non-clone 24 protein-derived peptides, namely mouse-derived PEPTIDE 2 (SEQ ID NO:19) composed of 14 amino acids and PEPTIDE 5 (SEQ ID NO:20), respectively, with PBS (product of Nissui Pharmaceutical). Each peptide solution was distributed in 50-µl portions into wells of a 96-well titer plate module (product of Nalge Nunc International), followed by 1 hour of incubation at 37° C. or peptide immobilization. Then, each module was washed with PBS, 0.5% bovine serum albumin-containing PBS was distributed in 200-µl portions into the wells, and incubation was carried out at 37° C. or 1 hour for blocking.

vii) Each rabbit anti-peptide serum prepared in the above step v) was 1000-fold diluted with PBS, the dilution was distributed in 50-µl portions into the wells of the blocked, peptide-immobilized module, and the reaction was allowed to proceed at 37° C. or 1 hour. Each module was washed with PBS, a solution prepared by 1500-fold diluting peroxidase-labeled goat anti-rabbit immunoglobulin (product of Biosource International) with PBS was distributed in 50-µl portions into the wells, and the reaction was allowed to proceed at 37° C. for 1 hour. After washing the module, ABTS peroxidase substrate (product of KPL) was added, the reaction was allowed to proceed at room temperature for 10 minutes, ABTS peroxidase stop solution (product of KPL) was added, and absorbance measurements were made at 405 nm. The results thus obtained are shown in FIG. 8.

These results revealed that the antibody obtained by immunization with PEPTIDE 4-coupled KLH reacts with the PEPTIDE 4-immobilized module alone, the antibody obtained by immunization with PEPTIDE 8-coupled KLH reacts with the PEPTIDE 8-immobilized module alone, and the antibody obtained by immunization with PEPTIDE 10-coupled KLH reacts with the PEPTIDE 10-immobilized module alone, but they do not react with any other peptide-immobilized modules.

From the results of this example, it could be established that antibodies can be obtained by immunizing rabbits with partial proteins of the murine clone 24 protein of the invention. It is evident that when these antibodies are used, immunodetection systems for assaying the antigens used for immunization or proteins derived from the antigens used for immunization can be constructed.

INDUSTRIAL APPLICABILITY

The polynucleotides and proteins of the invention are respectively polynucleotides and proteins extractable from cells within 12 hours, in particular around 6 hours, after the start of adipocyte differentiation induction and are novel as polynucleotides and proteins capable of being activated within 12 hours from the start of adipocyte differentiation induction.

These polynucleotides and proteins are substances very useful in elucidating the mechanisms of obesity and further properly understanding the state of progress of obesity and utilizing the findings thus obtained in the prevention or treatment of obesity.

The polynucleotides of the invention, the proteins or peptides deducible from the polynucleotides, and antibodies, antagonists or agonists to or of these peptides are useful in the treatment and diagnosis of such lifestyle-related diseases as diabetes, hypertension and arteriosclerosis.

The invention claimed is:

1. An isolated polynucleotide comprising a base sequence at least 98% homologous to the base sequence shown under SEQ ID NO:1, whereby the polynucleotide encoding a protein having a function to promote adipocyte differentiation and having a property such that it can be activated within 12 hours after the start of adipocyte differentiation induction.

2. An isolated polynucleotide comprising a base sequence identical to the base sequence shown under SEQ ID NO:1, whereby the polynucleotide encoding a protein having a function to promote adipocyte differentiation and having a property such that it can be activated within 12 hours after the start of adipocyte differentiation induction.

3. An isolated polynucleotide comprising a base sequence identical or at least 98% homologous to that portion of the base sequence shown under SEQ ID NO:1 which covers from the base No. 100 to the base No. 2520, whereby the polynucleotide encoding a protein having a function to promote adipocyte differentiation and having a property such that it can be activated within 12 hours after the start of adipocyte differentiation induction.

4. An isolated polynucleotide as set forth in claim 1, which is a DNA or RNA.

5. An isolated protein comprises an amino acid sequence at least 96% homologous to the protein specified under SEQ ID NO:2 all over the full length thereof, whereby the protein having a function to promote adipocyte differentiation and being capable of being activated within 12 hours from the start of adipose differentiation induction.

6. An isolated protein identical to the protein specified under SEQ ID NO:2 all over the full length thereof, whereby the protein having a function to promote adipocyte differentiation and being capable of being activated within 12 hours from the start of adipose differentiation induction.

7. A recombinant vector containing a polynucleotide as set forth in claim 1.

8. A transformant harboring the recombinant vector of claim 7.

9. A method of producing proteins which comprises culturing the transformant of claim 8 under conditions sufficient for the formation of the protein of claim 5 and recovering the protein from the culture medium or the transformant.

10. A pharmaceutical composition which comprises an isolated polynucleotide comprising a base sequence identical or at least 98% homologous to the base sequence shown under SEQ ID NO:1, whereby the polynucleotide encoding a protein having a function to promote adipocyte differentiation and having a property such that it can be activated within 12 hours after the start of adipocyte differentiation induction, and a pharmaceutically acceptable carrier.

11. A pharmaceutical composition which comprises an isolated polynucleotide comprising a base sequence identical or at least 98% homologous to the base sequence shown under SEQ ID NO:1, whereby the polynucleotide encoding a protein having a function to promote adipocyte differentiation and having a property such that it can be activated within 12 hours after the start of adipocyte differentiation induction, and a pharmaceutically acceptable carrier whereby the pharmaceutical composition is utilized for treating lifestyle-related diseases selected from the group consisting of obesity, hypertension, hyperlipidemia, diabetes, arteriosclerosis related heart diseases and cerebral apoplexy.

12. A pharmaceutical composition which comprises an isolated protein comprising an amino acid sequence identical or at least 96% homologous to the protein specified under SEQ ID NO:2 all over the full length thereof, whereby the protein having a function to promote adipocyte differentiation and capable of being activated within 12 hours from the start of adipose differentiation induction, and a pharmaceutically acceptable carrier.

13. A pharmaceutical composition which comprises an isolated protein comprising an amino acid sequence identical or at least 96% homologous to the protein specified under SEQ ID NO:2 all over the full length thereof, whereby the protein having a function to promote adipocyte differentiation and capable of being activated within 12 hours from the start of adipose differentiation induction, and a pharmaceutically acceptable carrier whereby the pharmaceutical composition is utilized for treating lifestyle-related diseases selected from the group consisting of obesity, hypertension, hyperlipidemia, diabetes, arteriosclerosis related heart diseases and cerebral apoplexy.

14. A diagnostic composition which comprises an isolated polynucleotide comprising a base sequence identical or at least 98% homologous to the base sequence shown under SEQ ID NO:1, whereby the polynucleotide encoding a protein having a function to promote adipocyte differentiation and having a property such that it can be activated within 12 hours after the start of adipocyte differentiation induction.

15. A diagnostic composition which comprises an isolated polynucleotide comprising a base sequence identical or at least 98% homologous to the base sequence shown under SEQ ID NO:1, whereby the polynucleotide encoding a protein having a function to promote adipocyte differentiation and having a property such that it can be activated within 12 hours after the start of adipocyte differentiation induction, whereby the diagnostic composition is utilized for detecting lifestyle-related diseases selected from the group consisting of obesity, hypertension, hyperlipidemia, diabetes, arteriosclerosis related heart diseases and cerebral apoplexy.

16. A diagnostic composition which comprises an isolated protein comprising an amino acid sequence identical or at least 96% homologous to the protein specified under SEQ ID NO:2 all over the full length thereof, whereby the protein having a function to promote adipocyte differentiation and capable of being activated within 12 hours from the start of adipose differentiation induction.

17. A diagnostic composition which comprises an isolated protein comprising an amino acid sequence identical or at least 96% homologous to the protein specified under SEQ ID NO:2 all over the full length thereof, whereby the protein having a function to promote adipocyte differentiation and capable of being activated within 12 hours from the start of adipose differentiation induction, whereby the diagnostic composition is utilized for detecting lifestyle-related diseases selected from the group consisting of obesity, hypertension, hyperlipidemia, diabetes, arteriosclerosis related heart diseases and cerebral apoplexy.

18. An isolated polynucleotide as set forth in claim 2, which is a DNA or RNA.

19. An isolated polynucleotide as set forth in claim 3, which is a DNA or RNA.

20. A recombinant vector containing a polynucleotide as set forth in claim 2.

21. A recombinant vector containing a polynucleotide as set forth in claim 3.

22. A method of producing proteins which comprises culturing the transformant of claim 8 under conditions sufficient for the formation of the protein of claim 6 and recovering the protein from the culture medium or the transformant.

* * * * *

SEQUENCE LISTING

<160> NUMBER OF SEQ ID NOS: 20

<210> SEQ ID NO 1
<211> LENGTH: 2782
<212> TYPE: DNA
<213> ORGANISM: murine adipocyte

```
<400> SEQUENCE: 1
gaaaggttgc gctcagtgca cgtgtgtctt ttccacccgg ctcctgcgtg ttcctctgtc      60
cgagtgatct tgtctgtggt actcctcgca ggcctaagga tgaaggcgag aagaaataaa     120
aagcaggtcc caagctttcg caagttgata aaaactagta aagtgaaact tgaaaacaaa     180
ttgaaaaata agcaatttaa acaacaaagt accatcaaga agtaccgaaa agagcagagg     240
aaactaaggc aagctgtaaa agatgctgtg tctaaaaaac ccattccgct ggaggaccca     300
aagagcaaac ggccagttaa aaggatggag agggaggagg acgaggagga agaagccctg     360
cctttggata tgatggacga ggatgaccta cagctgatga aggatttagg acaaaaggca     420
tcttttctca caagagatct ctcttctagt gaaccagtcc atatcaagaa acgaaagcat     480
gagagtgtga tagagaaata tgaaaaagtg ccaagaactc tgcaaaccgc accggagaag     540
gagttgattc acctgctccc tatcaaggac aagagtggca tcatccctca ggctcgggag     600
aagccggtca ctgacttgca gcaagaagag gaggctgagg aagagctgga agatgaggaa     660
gaggtcattg aagaccccag gaaggagctg accatagaag agcatgtgat cgagagaaag     720
aagaaactgc aggacaagaa aatacagatt gcagccttag catctgctat tctgtcagat     780
ccagaaagtc atattaaaaa actgaaagag ttgcgttcca tgctgatgga gcaggaccct     840
gatgtggctg tcactgtccg gaagttggtt atcatctcac tgatggagct gtttaaggac     900
atcactccct cgtataaaat ccggcctcta accgaagcag aaaaatctac caagattcgt     960
aaagaaaccc agaagttaag agaatttgaa gaaggcctgg ttagccaata caaattttat    1020
ttggaaaatc tggagcaaat agttaaagac tggaagcaaa ggaagctgaa gaagagcaac    1080
gtggtgtcct taaaggccta caagggctgg gctgaagtgg cagtgaagag cctgtgtgag    1140
ctgttggtgg ccctgcccca ttttaacttt cacaacaaca tcattgtact gattgtccct    1200
ctgatgaacg atgggtcaaa accggtatct gaaatgtgtt gcgaagcagt aaagaaactc    1260
tttaaacaag ataaattagg ccaagcttct ctgggtgtca ttaaagtcat ctctggtttt    1320
gtaaagggca gaaattacga agttaggcca gagatgttaa aaacatttt atgcctgcgg    1380
atcaaggagg tagaagtgaa aaagatacag aggacatta acaagcccaa aaggttcatg    1440
actttcaagg agaagagaaa aactctatca agaatgcaaa gaaagtggaa gaaagcagaa    1500
gagaaactag agcgggaact tcgggaggcc gaagcttcgg aaagcactga gaaaagctg     1560
aaactgcaca ccgagactct gaatattgtg tttgtgacct acttcagaat actgaagaag    1620
gcccagaagt cacctcttct gccagcggtt ctagaaggcc ttgccaagtt tgcacatctt    1680
ataaatgtgg agttttttga tgatttatta gtggttcttc ataccctcat tgagtctggg    1740
gagctaagtt atcaagaaag tctccactgt gttcaaactg cttttcatat tctttctgga    1800
caaggtgatg ttttaaatat tgacccgatg aaattctata cacatctcta caagacactg    1860
ttcacattac atgcaggtgc caccaacgac ggcattgaga ttgtgctcca ctgcctcgat    1920
gtcatgctaa gcaagcgcag aaagcaggtt tctcatcagc gagctcttgc cttcatcaaa    1980
cgcctttgta cacttgctct gcaggttctt ccaaattcaa gcattggcct tttagcaact    2040
accaggatat tgatgcatac ttttcccaga acagatctct tgcttgataa cgagtctcag    2100
ggcagcgggg tgtttctacc tgagctggag gagccagagt actgtaatgc acagaacacc    2160
gcactgtggg agctgcacac gcttcggaga cattaccatc ccattgtgcg aaggtttgca    2220
gcacatctgc ttgctggggc accatccgaa ggctctgagg ccctcaagcc cgagctgagc    2280
```

```
cgaagatctg cagttgaact ttttgagact tacagcatgg cagcaatgac attcaatccg    2340
cctgttgaat cttcacactc caaaaggaag gataaatttt taccaggaga ctcatttttg    2400
aatgaagatt taaatcaact aatcaaaaga tactgtaatg aagctgctcc tgagacaccg    2460
ctggatttcg ccaagtgttt ggaaagctca tcccggcagt acagagtgaa tggactgtct    2520
tagatatctg catgtgcatg gcagagacac aaggatatgt gagggcctgt ttctgtttgt    2580
acaaggaaga cttcctaaga atgattgaga actggagcag ggccacagaa gaccctgctc    2640
attggcttgc ttttcatgcc ttgctcggcc tagccttttt atacagtcca caccaacttg    2700
tccaggaatg gcactgccca tcagtcatga aatctacaaa tgccctgcag acatgccata    2760
gtctagtctg tggaggcagt cc                                             2782
```

<210> SEQ ID NO 2
<211> LENGTH: 807
<212> TYPE: PRT
<213> ORGANISM: murine adipocyte

<400> SEQUENCE: 2

```
Met Lys Ala Arg Arg Asn Lys Lys Gln Val Pro Ser Phe Arg Lys Leu
1               5                  10                  15

Ile Lys Thr Ser Lys Val Lys Leu Glu Asn Lys Leu Lys Asn Lys Gln
            20                  25                  30

Phe Lys Gln Gln Ser Thr Ile Lys Lys Tyr Arg Lys Glu Gln Arg Lys
        35                  40                  45

Leu Arg Gln Ala Val Lys Asp Ala Val Ser Lys Pro Ile Pro Leu
    50                  55                  60

Glu Asp Pro Lys Ser Lys Arg Pro Val Lys Met Glu Arg Glu Glu
65                  70                  75                  80

Asp Glu Glu Glu Glu Ala Leu Pro Leu Asp Met Met Asp Glu Asp Asp
                85                  90                  95

Leu Gln Leu Met Lys Asp Leu Gly Gln Lys Ala Ser Phe Leu Thr Arg
            100                 105                 110

Asp Leu Ser Ser Glu Pro Val His Ile Lys Lys Arg Lys His Glu
        115                 120                 125

Ser Val Ile Glu Lys Tyr Glu Lys Val Pro Arg Thr Leu Gln Thr Ala
    130                 135                 140

Pro Glu Lys Glu Leu Ile His Leu Leu Pro Ile Lys Asp Lys Ser Gly
145                 150                 155                 160

Ile Ile Pro Gln Ala Arg Glu Lys Pro Val Thr Asp Leu Gln Gln Glu
                165                 170                 175

Glu Glu Ala Glu Glu Glu Leu Glu Asp Glu Glu Val Ile Glu Asp
            180                 185                 190

Pro Arg Lys Glu Leu Thr Ile Glu Glu His Val Ile Glu Arg Lys Lys
        195                 200                 205

Lys Leu Gln Asp Lys Lys Ile Gln Ile Ala Ala Leu Ala Ser Ala Ile
    210                 215                 220

Leu Ser Asp Pro Glu Ser His Ile Lys Lys Leu Lys Glu Leu Arg Ser
225                 230                 235                 240

Met Leu Met Glu Gln Asp Pro Asp Val Ala Val Thr Val Arg Lys Leu
                245                 250                 255

Val Ile Ile Ser Leu Met Glu Leu Phe Lys Asp Ile Thr Pro Ser Tyr
            260                 265                 270

Lys Ile Arg Pro Leu Thr Glu Ala Glu Lys Ser Thr Lys Ile Arg Lys
        275                 280                 285
```

```
Glu Thr Gln Lys Leu Arg Glu Phe Glu Gly Leu Val Ser Gln Tyr
    290                 295                 300
Lys Phe Tyr Leu Glu Asn Leu Glu Gln Ile Val Lys Asp Trp Lys Gln
305                 310                 315                 320
Arg Lys Leu Lys Lys Ser Asn Val Val Ser Leu Lys Ala Tyr Lys Gly
            325                 330                 335
Leu Ala Glu Val Ala Val Lys Ser Leu Cys Glu Leu Val Ala Leu
            340                 345                 350
Pro His Phe Asn Phe His Asn Asn Ile Ile Val Leu Ile Val Pro Leu
            355                 360                 365
Met Asn Asp Gly Ser Lys Pro Val Ser Glu Met Cys Cys Glu Ala Val
370                 375                 380
Lys Lys Leu Phe Lys Gln Asp Lys Leu Gly Gln Ala Ser Leu Gly Val
385                 390                 395                 400
Ile Lys Val Ile Ser Gly Phe Val Lys Gly Arg Asn Tyr Glu Val Arg
            405                 410                 415
Pro Glu Met Leu Lys Thr Phe Leu Cys Leu Arg Ile Lys Glu Val Glu
            420                 425                 430
Val Lys Lys Asp Thr Glu Asp Ile Asn Lys Pro Lys Arg Phe Met Thr
435                 440                 445
Phe Lys Glu Lys Arg Lys Thr Leu Ser Arg Met Gln Arg Lys Trp Lys
450                 455                 460
Lys Ala Glu Glu Lys Leu Glu Arg Glu Leu Arg Glu Ala Glu Ala Ser
465                 470                 475                 480
Glu Ser Thr Glu Lys Lys Leu Lys Leu His Thr Glu Thr Leu Asn Ile
            485                 490                 495
Val Phe Val Thr Tyr Phe Arg Ile Leu Lys Lys Ala Gln Lys Ser Pro
            500                 505                 510
Leu Leu Pro Ala Val Leu Glu Gly Leu Ala Lys Phe Ala His Leu Ile
            515                 520                 525
Asn Val Glu Phe Phe Asp Asp Leu Leu Val Val Leu His Thr Leu Ile
            530                 535                 540
Glu Ser Gly Glu Leu Ser Tyr Gln Glu Ser Leu His Cys Val Gln Thr
545                 550                 555                 560
Ala Phe His Ile Leu Ser Gly Gln Gly Asp Val Leu Asn Ile Asp Pro
            565                 570                 575
Met Lys Phe Tyr Thr His Leu Tyr Lys Thr Leu Phe Thr Leu His Ala
            580                 585                 590
Gly Ala Thr Asn Asp Gly Ile Glu Ile Val Leu His Cys Leu Asp Val
            595                 600                 605
Met Leu Ser Lys Arg Lys Gln Val Ser His Gln Arg Ala Leu Ala
610                 615                 620
Phe Ile Lys Arg Leu Cys Thr Leu Ala Leu Gln Val Leu Pro Asn Ser
625                 630                 635                 640
Ser Ile Gly Leu Leu Ala Thr Thr Arg Ile Leu Met His Thr Phe Pro
            645                 650                 655
Arg Thr Asp Leu Leu Leu Asp Asn Glu Ser Gln Gly Ser Gly Val Phe
            660                 665                 670
Leu Pro Glu Leu Glu Glu Pro Gly Tyr Cys Asn Ala Gln Asn Thr Ala
            675                 680                 685
Leu Trp Glu Leu His Thr Leu Arg Arg His Tyr His Pro Ile Val Arg
            690                 695                 700
```

```
Arg Phe Ala Ala His Leu Leu Ala Gly Ala Pro Ser Glu Gly Ser Glu
705                 710                 715                 720

Ala Leu Lys Pro Glu Leu Ser Arg Arg Ser Ala Val Glu Leu Phe Glu
            725                 730                 735

Thr Tyr Ser Met Ala Ala Met Thr Phe Asn Pro Pro Val Glu Ser Ser
        740                 745                 750

His Ser Lys Arg Lys Asp Lys Phe Leu Pro Gly Asp Ser Phe Leu Asn
    755                 760                 765

Glu Asp Leu Asn Gln Leu Ile Lys Arg Tyr Cys Asn Glu Ala Ala Pro
770                 775                 780

Glu Thr Pro Leu Asp Phe Ala Lys Cys Leu Glu Ser Ser Ser Arg Gln
785                 790                 795                 800

Tyr Arg Val Asn Gly Leu Ser
                805

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
gccggcattc atttaaggcc                                                    20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
cttcgcatga acaggctcac                                                    20

<210> SEQ ID NO 5
<211> LENGTH: 18
<212> TYPE: DNA
<213> ORGANISM: Artificial
<220> FEATURE:
<223> OTHER INFORMATION: primer

<400> SEQUENCE: 5
cagatcccaa gctttcgc                                                      18

<210> SEQ ID NO 6
<211> LENGTH: 18
<212> TYPE: DNA
<213> ORGANISM: Artificial
<220> FEATURE:
<223> OTHER INFORMATION: primer

<400> SEQUENCE: 6
agcaaacttg gcaagacc                                                      18

<210> SEQ ID NO 7
<211> LENGTH: 18
<212> TYPE: DNA
<213> ORGANISM: Artificial
<220> FEATURE:
<223> OTHER INFORMATION: primer

<400> SEQUENCE: 7
```

```
aagaaggccc agaggtca                                                  18

<210> SEQ ID NO 8
<211> LENGTH: 18
<212> TYPE: DNA
<213> ORGANISM: Artificial
<220> FEATURE:
<223> OTHER INFORMATION: primer

<400> SEQUENCE: 8
gtccactgac ttcattcc                                                  18

<210> SEQ ID NO 9
<211> LENGTH: 2451
<212> TYPE: DNA
<213> ORGANISM: human adipocyte

<400> SEQUENCE: 9
gccggcattc atttaaggcc taaggatgaa ggcgagaaga aataaaaaac agatcccaag      60
ctttcgcaag ttaataaaaa ctagtaaagt caaacttgaa acaagctaaa aaataagca     120 gtttaaacaa caaagcactc tcaagaagta ccgaaaagaa cagaggaaac taaggcaagc    180
tgtgaaagat gctgtgtcta agaaacccat tccattggag aacccaaagg aaaagcgacc    240
aggtaaaagg attgagaggg aagaagagga agaagaagaa gcccttcctt tagatatgat    300
ggatgaagat gacttacagt taatgaagga tttaggacaa agagtatctt ttctaacaag    360
agatctttct tctagtgagc ctgttcatgc gaagaaacgg aagcatgaac gcattataga    420
taaatatgaa aaaataccaa gaactctgca aactgcacca gagaaggaac tgattcattt    480
acttcctatc aaagataaaa gtggtataat cccacagact agggagaagc cagttactga    540
tagtaacaaa gatgaagagg atcaagaaga agagagggaa cttgaggaag atcattga     600 agatcctatt caagagctga ccatagaaga acatttgatt gagagaaaga gaaaattaca    660
ggagaagaag atgcatattg cagccttggc atctgccata ttatcagatc cagaaaataa    720
tattaaaaaa ttgaaagaat tacgttctat gttgatggaa caagatcctg atgtggctgt    780
tactgttcga aagctggtaa ttgtttctct gatggagtta tttaaagata ttactccttc    840
atataaaatc cggccccctca cagaagcaga aaaatctact aagacccgaa agaaaccca    900 gaagttaaga gaatttgaag aaggcctggt tagccaatac aagttttatt tggaaaatct    960
ggaacaaatg gttaaagatt ggaagcagag gaagctgaag aaaagtaatg tagtttcctt   1020
aaaggcatac aaaggactgg cagaagtcgc tgtgaagagc ttgtgtgagc tgttggtggc   1080
actacctcat tttaactttc acaacaacat catcgtattg attgtccctc tcatgaatga   1140
catgtcaaaa ttgatatctg aaatgtgttg tgaagctgtg aagaaactct ttaagcaaga   1200
taaattaggc caggcttctc ttggtgtaat taaagtgatt tctggtttg tgaagggcag    1260 aaaattacgaa gttaggccag agatgttaaa acatttta tgcctaagaa tcaaggaagt   1320
agaagtgaaa aaagatacag aagacattaa taaaccaaaa aaatttatga ctttcaaaga   1380
aaagagaaaa tctctatcaa gaatgcagag aaagtggaaa aaagcagaag agaaactaga   1440
gcgagagctt cgagaggcag aagcttcaga gagtactgag aaaaaactta aactgcacac   1500
agagactctg aatattgtgt tgtaacccta cttcagaata ttgaagaagg cccagaggtc   1560
acctctcctg ccagcagttc tagaaggtct tgccaagttt gctcaccttta taaatgtgga   1620 atttttgat gatctgttag tagttcttca tactctcatt gagtcggtg acctaagcta     1680 tcaagaaagt cttcactgtg tccagactgc ttttcatatt ctttctggac aaggtgatgt   1740
```

-continued

```
tctgaatatt gatccattga aattctacac acatctctac aaaacactgt tcaaattaca   1800
tgcaggtgct accaatgaag gtgttgagat tgtactccag tgccttgatg tcatgctaac   1860
taagcgcaga aagcaagttt ctcagcagcg agctcttgcc ttcatcaaac gcctttgtac   1920
ccttgctctt catgttcttc caaattcaag tattggcatt ttagcaacta ccagaatatt   1980
aatgcatact ttccccaaaa cagatctact gcttgacagt gaatctcagg gaagtggagt   2040
tttccttcct gaactggatg agcctgagta ctgcaatgct cagaacactg ctctgtggga   2100
actgcatgct ctgcggaggc attatcatcc catagtgcag agatttgcag cccacctgat   2160
cgctggagca ccttctgaag gctctggagc actcaaacca gagttgagtc aagatctgc   2220 tactgaactt tttgaggcat atagcatggc agaaatgaca ttcaatcctc ctgttgaatc   2280
ttcaaacccc aaaataaagg gtaaattttt acaaggggat tcattttgga atgaagattt   2340
aaatcagcta atcaaaagat actccagtga agttgctact gaatcgcctc tggatttcac   2400
gaaatatttg aaaacatcac tacactagta gaggaatgaa gtcagtggac t            2451
```

<210> SEQ ID NO 10
<211> LENGTH: 800
<212> TYPE: PRT
<213> ORGANISM: human adipocyte

<400> SEQUENCE: 10

```
Met Lys Ala Arg Arg Asn Lys Lys Gln Ile Pro Ser Phe Arg Lys Leu
1               5                   10                  15

Ile Lys Thr Ser Lys Val Lys Leu Glu Asn Lys Leu Lys Asn Lys Gln
                20                  25                  30

Phe Lys Gln Gln Ser Thr Leu Lys Lys Tyr Arg Lys Glu Gln Arg Lys
            35                  40                  45

Leu Arg Gln Ala Val Lys Asp Ala Val Ser Lys Pro Ile Pro Leu
        50                  55                  60

Glu Asn Pro Lys Glu Lys Arg Pro Gly Lys Arg Ile Glu Arg Glu Glu
65                  70                  75                  80

Glu Glu Glu Glu Glu Ala Leu Pro Leu Asp Met Met Asp Glu Asp Asp
                85                  90                  95

Leu Gln Leu Met Lys Asp Leu Gly Gln Arg Val Ser Phe Leu Thr Arg
                100                 105                 110

Asp Leu Ser Ser Ser Glu Pro Val His Ala Lys Lys Arg Lys His Glu
            115                 120                 125

Arg Ile Ile Asp Lys Tyr Glu Lys Ile Pro Arg Thr Leu Gln Thr Ala
        130                 135                 140

Pro Glu Lys Glu Leu Ile His Leu Leu Pro Ile Lys Asp Lys Ser Gly
145                 150                 155                 160

Ile Ile Pro Gln Thr Arg Glu Lys Pro Val Thr Asp Ser Asn Lys Asp
                165                 170                 175

Glu Glu Asp Gln Glu Glu Glu Arg Glu Leu Glu Glu Ile Ile Glu
                180                 185                 190

Asp Pro Ile Gln Glu Leu Thr Ile Glu Glu His Leu Ile Glu Arg Lys
        195                 200                 205

Lys Lys Leu Gln Glu Lys Lys Met His Ile Ala Ala Leu Ala Ser Ala
    210                 215                 220

Ile Leu Ser Asp Pro Glu Asn Asn Ile Lys Lys Leu Lys Glu Leu Arg
225                 230                 235                 240

Ser Met Leu Met Glu Gln Asp Pro Asp Val Ala Val Thr Val Arg Lys
```

-continued

```
                245                 250                 255
Leu Val Ile Val Ser Leu Met Glu Leu Phe Lys Asp Ile Thr Pro Ser
                260                 265                 270
Tyr Lys Ile Arg Pro Leu Thr Glu Ala Glu Lys Ser Thr Lys Thr Arg
                275                 280                 285
Lys Glu Thr Gln Lys Leu Arg Glu Phe Glu Glu Gly Leu Val Ser Gln
                290                 295                 300
Tyr Lys Phe Tyr Leu Glu Asn Leu Glu Gln Met Val Lys Asp Trp Lys
305                 310                 315                 320
Gln Arg Lys Leu Lys Lys Ser Asn Val Val Ser Leu Lys Ala Tyr Lys
                325                 330                 335
Gly Leu Ala Glu Val Ala Val Lys Ser Leu Cys Glu Leu Leu Val Ala
                340                 345                 350
Leu Pro His Phe Asn Phe His Asn Asn Ile Ile Val Leu Ile Val Pro
                355                 360                 365
Leu Met Asn Asp Met Ser Lys Leu Ile Ser Glu Met Cys Cys Glu Ala
                370                 375                 380
Val Lys Lys Leu Phe Lys Gln Asp Lys Leu Gly Gln Ala Ser Leu Gly
385                 390                 395                 400
Val Ile Lys Val Ile Ser Gly Phe Val Lys Gly Arg Asn Tyr Glu Val
                405                 410                 415
Arg Pro Glu Met Leu Lys Thr Phe Leu Cys Leu Arg Ile Lys Glu Val
                420                 425                 430
Glu Val Lys Lys Asp Thr Glu Asp Ile Asn Lys Pro Lys Lys Phe Met
                435                 440                 445
Thr Phe Lys Glu Lys Arg Lys Ser Leu Ser Arg Met Gln Arg Lys Trp
                450                 455                 460
Lys Lys Ala Glu Glu Lys Leu Glu Arg Glu Leu Arg Glu Ala Glu Ala
465                 470                 475                 480
Ser Glu Ser Thr Glu Lys Lys Leu Lys Leu His Thr Glu Thr Leu Asn
                485                 490                 495
Ile Val Phe Val Thr Tyr Phe Arg Ile Leu Lys Lys Ala Gln Arg Ser
                500                 505                 510
Pro Leu Leu Pro Ala Val Leu Glu Gly Leu Ala Lys Phe Ala His Leu
                515                 520                 525
Ile Asn Val Glu Phe Phe Asp Asp Leu Leu Val Val Leu His Thr Leu
                530                 535                 540
Ile Glu Ser Gly Asp Leu Ser Tyr Gln Glu Ser Leu His Cys Val Gln
545                 550                 555                 560
Thr Ala Phe His Ile Leu Ser Gly Gln Gly Asp Val Leu Asn Ile Asp
                565                 570                 575
Pro Leu Lys Phe Tyr Thr His Leu Tyr Lys Thr Leu Phe Lys Leu His
                580                 585                 590
Ala Gly Ala Thr Asn Glu Gly Val Glu Ile Val Leu Gln Cys Leu Asp
                595                 600                 605
Val Met Leu Thr Lys Arg Arg Lys Gln Val Ser Gln Gln Arg Ala Leu
                610                 615                 620
Ala Phe Ile Lys Arg Leu Cys Thr Leu Ala Leu His Val Leu Pro Asn
625                 630                 635                 640
Ser Ser Ile Gly Ile Leu Ala Thr Thr Arg Ile Leu Met His Thr Phe
                645                 650                 655
Pro Lys Thr Asp Leu Leu Asp Ser Glu Ser Gln Gly Ser Gly Val
                660                 665                 670
```

```
Phe Leu Pro Glu Leu Asp Glu Pro Glu Tyr Cys Asn Ala Gln Asn Thr
            675                 680                 685

Ala Leu Trp Glu Leu His Ala Leu Arg Arg His Tyr His Pro Ile Val
        690                 695                 700

Gln Arg Phe Ala Ala His Leu Ile Ala Gly Ala Pro Ser Glu Gly Ser
705                 710                 715                 720

Gly Ala Leu Lys Pro Glu Leu Ser Arg Arg Ser Ala Thr Glu Leu Phe
                725                 730                 735

Glu Ala Tyr Ser Met Ala Glu Met Thr Phe Asn Pro Pro Val Glu Ser
            740                 745                 750

Ser Asn Pro Lys Ile Lys Gly Lys Phe Leu Gln Gly Asp Ser Phe Leu
        755                 760                 765

Asn Glu Asp Leu Asn Gln Leu Ile Lys Arg Tyr Ser Ser Glu Val Ala
    770                 775                 780

Thr Glu Ser Pro Leu Asp Phe Thr Lys Tyr Leu Lys Thr Ser Leu His
785                 790                 795                 800

<210> SEQ ID NO 11
<211> LENGTH: 22
<212> TYPE: DNA
<213> ORGANISM: Artificial
<220> FEATURE:
<223> OTHER INFORMATION: upper layer primer

<400> SEQUENCE: 11
cgcaggccta aggatgaagg cg                                           22

<210> SEQ ID NO 12
<211> LENGTH: 24
<212> TYPE: DNA
<213> ORGANISM: artificial
<220> FEATURE:
<223> OTHER INFORMATION: lower layer

<400> SEQUENCE: 12
cagggtcttc tgtggccctg ctcc                                         24

<210> SEQ ID NO 13
<211> LENGTH: 17
<212> TYPE: PRT
<213> ORGANISM: murine adipocyte

<400> SEQUENCE: 13

Lys Asp Ile Thr Pro Ser Tyr Lys Ile Arg Pro Leu Thr Glu Ala Glu
1               5                   10                  15

Lys

<210> SEQ ID NO 14
<211> LENGTH: 18
<212> TYPE: PRT
<213> ORGANISM: artificial
<220> FEATURE:
<223> OTHER INFORMATION: introducing cys

<400> SEQUENCE: 14

Cys Lys Asp Ile Thr Pro Ser Tyr Lys Ile Arg Pro Leu Thr Glu Ala
1               5                   10                  15

Glu Lys

<210> SEQ ID NO 15
```

```
<211> LENGTH: 21
<212> TYPE: PRT
<213> ORGANISM: murine adioicyte

<400> SEQUENCE: 15

Leu Arg Ile Lys Glu Val Glu Val Lys Lys Asp Thr Glu Asp Ile Asn
1               5                   10                  15

Lys Pro Lys Arg Phe
            20

<210> SEQ ID NO 16
<211> LENGTH: 22
<212> TYPE: PRT
<213> ORGANISM: artificial
<220> FEATURE:
<223> OTHER INFORMATION: introducing cys

<400> SEQUENCE: 16

Cys Leu Arg Ile Lys Glu Val Glu Val Lys Lys Asp Thr Glu Asp Ile
1               5                   10                  15

Asn Lys Pro Lys Arg Phe
            20

<210> SEQ ID NO 17
<211> LENGTH: 16
<212> TYPE: PRT
<213> ORGANISM: murine adpocyte

<400> SEQUENCE: 17

Glu Ser Ser His Ser Lys Arg Lys Asp Lys Phe Leu Pro Gly Asp Ser
1               5                   10                  15

<210> SEQ ID NO 18
<211> LENGTH: 17
<212> TYPE: PRT
<213> ORGANISM: artificial
<220> FEATURE:
<223> OTHER INFORMATION: introducing cys

<400> SEQUENCE: 18

Cys Glu Ser Ser His Ser Lys Arg Lys Asp Lys Phe Leu Pro Gly Asp
1               5                   10                  15

Ser

<210> SEQ ID NO 19
<211> LENGTH: 14
<212> TYPE: PRT
<213> ORGANISM: murine

<400> SEQUENCE: 19

Glu Val Ser Gly Glu Asp Ser Glu Glu Lys Asp Asn Arg Lys
1               5                   10

<210> SEQ ID NO 20
<211> LENGTH: 13
<212> TYPE: PRT
<213> ORGANISM: murine

<400> SEQUENCE: 20

Glu Thr Gly Ile Asp Asp Ile Pro Asp Val Lys Asn Asp
1               5                   10
```